United States Patent
Ripka et al.

(10) Patent No.: US 8,481,532 B2
(45) Date of Patent: Jul. 9, 2013

(54) PDE-10 INHIBITORS

(75) Inventors: Amy Ripka, Reading, MA (US);
Gideon Shapiro, Gainesville, FL (US);
Richard Chesworth, Boston, MA (US)

(73) Assignee: EnVivo Pharmaceuticals, Inc., Watertown, MA (US)

( * ) Notice: Subject to any disclaimer, the term of this patent is extended or adjusted under 35 U.S.C. 154(b) by 128 days.

(21) Appl. No.: 13/002,922

(22) PCT Filed: Jul. 9, 2009

(86) PCT No.: PCT/US2009/050055
§ 371 (c)(1),
(2), (4) Date: Apr. 4, 2011

(87) PCT Pub. No.: WO2010/006130
PCT Pub. Date: Jan. 14, 2010

(65) Prior Publication Data
US 2011/0178083 A1    Jul. 21, 2011

Related U.S. Application Data

(60) Provisional application No. 61/079,179, filed on Jul. 9, 2008.

(51) Int. Cl.
*C07D 401/14*    (2006.01)
*C07D 217/04*    (2006.01)
*A61K 31/47*    (2006.01)

(52) U.S. Cl.
USPC .......... 514/234.5; 514/233.8; 514/235.2; 514/253.04; 514/253.05; 514/300; 514/307; 514/311; 514/367; 514/375; 514/394; 514/406; 544/122; 544/127; 544/128; 544/135; 544/137; 544/139; 544/140; 544/362; 544/363; 546/122; 546/146; 546/175; 548/180; 548/217; 548/304.4; 548/361.1

(58) Field of Classification Search
None
See application file for complete search history.

(56) References Cited

U.S. PATENT DOCUMENTS
2003/0032579 A1    2/2003    Lebel et al.

FOREIGN PATENT DOCUMENTS
WO    WO 2009/086303    7/2009

OTHER PUBLICATIONS

International Search Report and Written Opinion, dated Mar. 8, 2010, issued in International Application No. PCT/US2009/050055.
STN search run Feb. 7, 2011 on compounds with RN 1164500-57-5, RN 1164497-92-0, RN 1164501-11-4, and RN 664974-63-4, 29 pp.
Fujishige et al. "Cloning and characterization of a novel human phosphodiesterase that hydrolyzes both cAMP and cGMP (PDE10A)" J. Biol. Chem. Jun. 1999,274, 18438-18445.
Handa et al. "Crystal structure of the GAF-B domain from human phosphodiesterase 10A complexed with its ligand, cAMP" J Biol. Chem. Jul. 2008, pp. 19657-19664.
Kostowski et. al "Papaverine drug induced stereotypy and catalepsy and biogenic aminesin the brain of the rat" Pharmacol. Biochem. Behav. Jul. 1976, 5, 15-17.
Loughney et al. "Isolation and characterization of PDE10A, a novel human 3',5'—cyclicnucleotide phosphodiesterase" Gene, Jun. 1999, vol. 234, No. 1. pp. 109-117.
Soderling and Beavo "Regulation of cAMP and cGMP signaling: New phosphodiesterases and new functions," Curr. Opin. Cell Biol., Apr. 2000, vol. 12, No. 2. pp. 174-179.
Soderling et al. "Isolation and characterization of a dual-substrate phosphodiesterase gene family: PDE10A" Proc. Natl Sci. Jun. 8, 1999, vol. 96, No. 12. pp. 7071-7076.

*Primary Examiner* — Zinna Northington Davis
(74) *Attorney, Agent, or Firm* — Wilmer Cutler Pickering Hale and Dorr LLP

(57) ABSTRACT

Vicinal substituted cyclopropyl compounds which are inhibitors of phosphodiesterase 10 are described as are processes, pharmaceutical compositions, pharmaceutical preparations and pharmaceutical use of the compounds in the treatment of mammals, including human(s) for central nervous system (CNS) disorders and other disorders which may affect CNS function, for example neurological, neurodegenerative and psychiatric disorders including, but not limited to, those comprising cognitive deficits or schizophrenic symptoms.

14 Claims, No Drawings

PDE-10 INHIBITORS

This application is the U.S. national stage under 35 USC §371 of International Application Number PCT/US2009/050055, filed on Jul. 9, 2009, which claims priority to U. S. Application No. 61/079,179, filed on Jul. 9, 2008, the entire contents of which is hereby incorporated by reference.

The disclosure relates to vicinal substituted cyclopropyl compounds which are inhibitors of phosphodiesterase 10. The disclosure further relates to processes, pharmaceutical compositions, pharmaceutical preparations and pharmaceutical use of the compounds in the treatment of mammals, including human(s) for central nervous system (CNS) disorders and other disorders which may affect CNS function. The disclosure also relates to methods for treating neurological, neurodegenerative and psychiatric disorders including, but not limited to, those comprising cognitive deficits or schizophrenic symptoms.

BACKGROUND

Cyclic phosphodiesterases are intracellular enzymes which, through the hydrolysis of cyclic nucleotides cAMP and cGMP, regulate the levels of these mono phosphate nucleotides which serve as second messengers in the signaling cascade of G-protein coupled receptors. In neurons, PDEs also play a role in the regulation of downstream cGMP and cAMP dependent kinases which phosphorylate proteins involved in the regulation of synaptic transmission and homeostasis. To date, eleven different PDE families have been identified which are encoded by 21 genes. The PDEs contain a variable N-terminal regulatory domain and a highly conserved C-terminal catalytic domain and differ in their substrate specificity, expression and localization in cellular and tissue compartments, including the CNS.

The discovery of a new PDE family, PDE10, was reported simultaneously by three groups in 1999 (Soderling et al. "Isolation and characterization of a dual-substrate phosphodiesterase gene family: PDE10A" *Proc. Natl Sci.* 1999, 96, 7071-7076; Loughney et al. "Isolation and characterization of PDE10A, a novel human 3',5'-cyclic nucleotide phosphodiesterase" *Gene* 1999, 234, 109-117; Fujishige et al. "Cloning and characterization of a novel human phosphodiesterase that hydrolyzes both cAMP and cGMP (PDE10A)" *J. Biol. Chem.* 1999, 274, 18438-18445). The human PDE10 sequence is highly homologous to both the rat and mouse variants with 95% amino acid identity overall, and 98% identity conserved in the catalytic region.

PDE10 is primarily expressed in the brain (caudate nucleus and putamen) and is highly localized in the medium spiny neurons of the striatum, which is one of the principal inputs to the basal ganglia. This localization of PDE10 has led to speculation that it may influence the dopaminergic and glutamatergic pathways both which play roles in the pathology of various psychotic and neurodegenerative disorders.

PDE10 hydrolyzes both cAMP ($K_m$=0.05 uM) and cGMP ($K_m$=3 uM) (Soderling et al. "Isolation and Characterization of a dual-substrate phosphodiesterase gene family: PDE10." *Proc. Natl. Sci. USA* 1999, 96(12), 7071-7076). In addition, PDE10 has a five-fold greater $V_{max}$ for cGMP than for cAMP and these in vitro kinetic data have lead to the speculation that PDE10 may act as a cAMP-inhibited cGMP phosphodiesterase in vivo (Soderling and Beavo "Regulation of cAMP and cGMP signaling: New phosphodiesterases and new functions," *Curr. Opin. Cell Biol.*, 2000, 12, 174-179).

PDE10 is also one of five phosphodiesterase members to contain a tandem GAF domain at their N-terminus. It is differentiated by the fact that the other GAF containing PDEs (PDE2, 5, 6, and 11) bind cGMP while recent data points to the tight binding of cAMP to the GAF domain of PDE10 (Handa et al. "Crystal structure of the GAF-B domain from human phosphodiesterase 10A complexed with its ligand, cAMP" *J. Biol. Chem.* 2008, May 13, ePub).

PDE10 inhibitors have been disclosed for the treatment of a variety of neurological and psychiatric disorders including Parkinson's disease, schizophrenia, Huntington's disease, delusional disorders, drug-induced psychoses, obsessive compulsive and panic disorders (US Patent Application 2003/0032579). Studies in rats (Kostowski et. al "Papaverine drug induced stereotypy and catalepsy and biogenic amines in the brain of the rat" *Pharmacol. Biochem. Behav.* 1976, 5, 15-17) have showed that papaverine, a selective PDE10 inhibitor, reduces apomorphine induced stereotypies and rat brain dopamine levels and increases haloperidol induced catalepsy. This experiment lends support to the use of a PDE10 inhibitor as an antipsychotic since similar trends are seen with known, marketed antipsychotics.

Antipsychotic medications are the mainstay of current treatment for schizophrenia. Conventional or classic antipsychotics, typified by haloperidol, were introduced in the mid-1950s and have a proven track record over the last half century in the treatment of schizophrenia. While these drugs are effective against the positive, psychotic symptoms of schizophrenia, they show little benefit in alleviating negative symptoms or the cognitive impairment associated with the disease. In addition, drugs such as haloperidol have extreme side effects such as extrapyramidal symptoms (EPS) due to their specific dopamine D2 receptor interaction. An even more severe condition characterized by significant, prolonged, abnormal motor movements known as tardive dyskinesia also may emerge with prolonged classic antipsychotic treatment.

The 1990s saw the development of several new drugs for schizophrenia, referred to as atypical antipsychotics, typified by risperidone and olanzapine and most effectively, clozapine. These atypical antipsychotics are generally characterized by effectiveness against both the positive and negative symptoms associated with schizophrenia, but have little effectiveness against cognitive deficiencies and persisting cognitive impairment remain a serious public health concern (Davis, J. M et al. "Dose response and dose equivalence of antipsychotics." *Journal of Clinical Psychopharmacology*, 2004, 24 (2), 192-208; Friedman, J. H. et al "Treatment of psychosis in Parkinson's disease: Safety considerations." *Drug Safety*, 2003, 26 (9), 643-659). In addition, the atypical antipsychotic agents, while effective in treating the positive and, to some degree, negative symptoms of schizophrenia, have significant side effects. For example, clozapine which is one of the most clinically effective antipsychotic drugs shows agranulocytosis in approximately 1.5% of patients with fatalities due to this side effect being observed. Other atypical antipsychotic drugs have significant side effects including metabolic side effects (type 2 diabetes, significant weight gain, and dyslipidemia), sexual dysfunction, sedation, and potential cardiovascular side effects that compromise their clinically effectiveness. In the large, recently published NIH sponsored CATIE study, (Lieberman et al "The Clinical Antipsychotic Trials Of Intervention Effectiveness (CATIE) Schizophrenia Trial: clinical comparison of subgroups with and without the metabolic syndrome." *Schizophrenia Research*, 2005, 80 (1), 9-43) 74% of patients discontinued use of their antipsychotic medication within 18 months due to a number of factors including poor tolerability or incomplete efficacy. Therefore, a substantial clinical need still exists for more effective and better tolerated antipsychotic mediations possibly through the use of PDE10 inhibitors.

BRIEF SUMMARY

Described herein are vicinal substituted cyclopropyl compounds of Formula (I) or (II) and pharmaceutically acceptable salts thereof, which are inhibitors of at least one phosphodiesterase 10

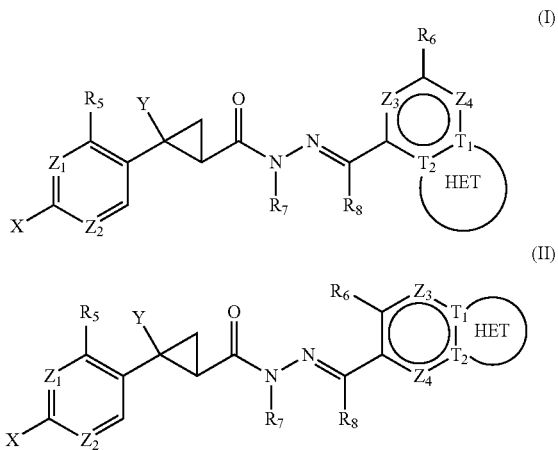

Wherein:

X is selected from hydrogen, halogen, $C_3$-$C_8$ alkyl, $C_1$-$C_4$ alkoxy, optionally substituted cycloalkyl, optionally substituted cycloalkyloxy, optionally substituted cycloalkylalkyl, optionally substituted cycloalkylalkoxy, optionally substituted heterocycloalkyl, optionally substituted heterocycloalkylalkyl, optionally substituted heterocycloalkyloxy, optionally substituted phenyl, optionally substituted heteroaryl, optionally substituted heteroaryloxy and optionally substituted heteroarylalkyl Y is selected from hydrogen, $C_3$-$C_8$ alkyl, $C_1$-$C_4$ alkoxy, optionally substituted cycloalkyl, optionally substituted cycloalkylalkyl, optionally substituted heterocycloalkyl, optionally substituted heterocycloalkylalkyl, optionally substituted phenyl or optionally substituted heteroaryl $T_1$ is C $T_2$ is C $Z_1$ is selected from $CR_1$ and N $Z_2$ is selected from $CR_2$ and N $Z_3$ is selected from $CR_3$ and N $Z_4$ is selected from $CR_4$ and N HET is selected from an optionally substituted monocyclic heteroaryl having 5 ring atoms selected from C, O, S and N provided the total number of ring heteroatoms is less than or equal to three and where no more than one of the total number of heteroatoms is oxygen or sulfur, an optionally substituted monocyclic heteroaryl having 6 atoms selected from C and N provided that not more than 2 ring atoms are N, and an optionally substituted monocyclic heterocycloalkyl.

$R_1$ is selected from hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido.

$R_2$ is selected from hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido.

$R_3$ is selected from hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido.

$R_4$ is selected from hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido.

$R_5$ is selected from hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido.

$R_6$ is selected from hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido.

$R_7$ is selected from hydrogen, $C_1$-$C_4$ alkyl and $C_3$-$C_6$ cycloalkyl.

$R_8$ is selected from hydrogen, $C_1$-$C_4$ alkyl and $C_3$-$C_6$ cycloalkyl.

In some embodiments, alkyl groups are fully saturated whether present on their own or as part of another group (e.g., alkylamino and alkylamido).

In certain embodiments, substituent groups are not further substituted.

In various embodiments, any group that is defined as being optionally substituted is independently singly or multiply substituted.

In various embodiments, any group that is defined as being optionally substituted is not substituted.

In one embodiment, X is selected from cycloalkyl, cycloalkyloxy, cycloalkylalkyl, cycloalkylalkoxy, heterocycloalkyl, heterocycloalkylalkyl, heterocycloalkyloxy, phenyl, heteroaryl, heteroaryloxy and heteroarylalkyl.

In another embodiment, X is selected from alkyl, cycloalkyl, cycloalkyloxy, cycloalkylalkyl and cycloalkylalkoxy.

In another embodiment, X is selected from halogen, $C_1$-$C_4$ alkoxy, alkyl, cycloalkyl, cycloalkyloxy, cycloalkylalkyl and cycloalkylalkoxy.

In another embodiment, X is selected from cycloalkyl, cycloalkyloxy, cycloalkylalkyl and cycloalkylalkoxy.

In an additional embodiment, X is selected from alkyl, heterocycloalkyl, heterocycloalkylalkyl and heterocycloalkyloxy.

In an additional embodiment, X is selected from alkyl, heterocycloalkyl, heterocycloalkylalkyl and heterocycloalkyloxy.

In a further embodiment, X is heterocycloalkyl.

In another embodiment, X is selected from heteroaryl, heteroaryloxy and heteroarylalkyl.

In another embodiment, X is selected from alkyl, phenyl and heteroaryl.

In another embodiment, X is selected from phenyl and heteroaryl.

In an additional embodiment, X is heteroaryl.

In an additional embodiment, X is phenyl.

In an additional embodiment, X is restricted phenyl.

In another embodiment, X is selected from a monocyclic heteroaryl having 5 ring atoms selected from C, O, S and N provided the total number of ring heteroatoms is less than or equal to four and where no more than one of the total number of heteroatoms is oxygen or sulfur, and a monocyclic heteroaryl having 6 atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, alkylsulfonyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl, 1,2,3-triazinyl, 1,2,4-triazinyl, 1,3,5-triazinyl, pyridinyl, pyrazinyl, pyridazinyl and pyrimidinyl.

In one embodiment, Y is hydrogen.

In another embodiment, Y is selected from alkyl and alkoxy.

In another embodiment, Y is selected from cycloalkyl, cycloalkylalkyl, cycloalkylalkoxy, heterocycloalkyl, heterocycloalkyloxy.

In another embodiment, Y is selected from cycloalkyl, cycloalkylalkyl and cycloalkylalkoxy.

In another embodiment, Y is selected from cycloalkyl, heterocycloalkyl and heterocycloalkyloxy.

In a further embodiment, Y is selected from phenyl and heteroaryl.

In an additional embodiment, Y is heteroaryl.

In another embodiment, Y is selected from phenyl, a monocyclic heteroaryl having 5 ring atoms selected from C, O, S and N provided the total number of ring heteroatoms is less than or equal to four and where no more than one of the total number of heteroatoms is oxygen or sulfur, and a monocyclic heteroaryl having 6 atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, alkylsulfonyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl, 1,2,3-triazinyl, 1,2,4-triazinyl, 1,3,5-triazinyl, pyridinyl, pyrazinyl, pyridazinyl and pyrimidinyl.

In another embodiment, Y is selected from a monocyclic aromatic ring having 5 ring atoms selected from C, O, S and N provided the total number of ring heteroatoms is less than or equal to four and where no more than one of the total number of heteroatoms is oxygen or sulfur, and a monocyclic aromatic ring having 6 atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxy, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl, 1,2,3-triazinyl, 1,2,4-triazinyl, 1,3,5-triazinyl, pyridinyl, pyrazinyl, pyridazinyl and pyrimidinyl.

In a further embodiment, Y is phenyl.

In another embodiment, Y is restricted phenyl.

In one embodiment $Z_1$ is $CR_1$.

In another embodiment $Z_1$ is N.

In one embodiment $Z_2$ is $CR_2$.

In another embodiment $Z_2$ is N.

In one embodiment $Z_3$ is $CR_3$.

In another embodiment $Z_3$ is N.

In one embodiment $Z_4$ is $CR_4$.

In another embodiment $Z_4$ is N.

In one embodiment, HET is selected from a monocyclic heteroaryl having 5 ring atoms selected from C, O, S and N provided the total number of ring heteroatoms is less than or equal to three and where no more than one of the total number of heteroatoms is oxygen or sulfur, and a monocyclic heteroaryl having 6 atoms selected from C and N provided that not more than 2 ring atoms are N, and where said ring may be optionally and independently substituted with up to two groups selected from $C_1$-$C_4$ alkyl, $C_3$-$C_6$ cycloalkyl, alkoxy, $C_3$-$C_6$ cycloalkyloxy, carboxy, halogen, nitro, alkylsulfonyl, amino, alkylamino, dialkylamino, amido, alkylamido, dialkylamido and cyano. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,3-oxadiazolyl, 1,2,3-thiadiazolyl, 1,2,3-triazinyl, 1,2,4-triazinyl, pyridinyl, pyrazinyl, pyridazinyl, pyrimidinyl and pyridin-2(1H)-onyl.

In another embodiment, HET is a monocyclic heteroaryl having 5 ring atoms selected from C, O, S and N provided the total number of ring heteroatoms is less than or equal to three and where no more than one of the total number of heteroatoms is oxygen or sulfur where said ring may be optionally and independently substituted with up to two groups selected from $C_1$-$C_4$ alkyl, $C_3$-$C_6$ cycloalkyl, alkoxy, $C_3$-$C_6$ cycloalkyloxy, carboxy, halogen, nitro, alkylsulfonyl, amino, alkylamino, dialkylamino, amido, alkylamido, dialkylamido and cyano. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,3-oxadiazolyl, 1,2,3-thiadiazolyl, 1,2,3-triazinyl and 1,2,4-triazinyl.

In another embodiment, HET is a monocyclic aromatic ring having 6 atoms selected from C and N provided that not more than 2 ring atoms are N, where said ring may be optionally and independently substituted with up to two groups selected from $C_1$-$C_4$ alkyl, $C_3$-$C_6$ cycloalkyl, alkoxy, $C_3$-$C_6$ cycloalkyloxy, carboxy, halogen, nitro, alkylsulfonyl, amino, alkylamino, dialkylamino, amido, alkylamido, dialkylamido and cyano. Examples include but are not limited to pyridinyl, pyrazinyl, pyridazinyl, pyrimidinyl and pyridin-2(1H)-onyl.

In an additional embodiment, HET is a monocyclic heterocycloalkyl.

In a further embodiment HET is a monocyclic heterocycloalkyl having only 6 ring atoms. Examples include, but are not limited to, morpholinyl, piperidinyl, piperazinyl N-Me-piperazinyl and pyranyl.

In another embodiment HET is a monocyclic heterocycloalkyl having only 5 ring atoms. Examples include, but are not limited to, tetrahydrofuranyl and pyrrolidinyl.

In another embodiment, HET is selected from, imidazolyl, thiazolyl, oxazolyl, pyridinyl, pyrmidinyl, pyrazinyl, triazolyl, pyrazolyl, cinnolinyl, piperidinyl, pyrrolidinyl, tetrahydrofuranyl, and pyranyl.

In another embodiment, $R_1$ is selected from hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_1$ is selected from halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_1$ is selected from hydrogen, alkoxy, halogen, cyano, alkylsulfonyl and nitro.

In one embodiment, $R_1$ is hydrogen.

In another embodiment, $R_2$ is selected from hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_2$ is selected from halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_2$ is selected from hydrogen, alkoxy, halogen, cyano, alkylsulfonyl and nitro.

In one embodiment, $R_2$ is hydrogen.

In another embodiment, $R_3$ is selected from hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_3$ is selected from halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_3$ is selected from hydrogen, alkoxy, halogen, cyano, alkylsulfonyl and nitro.

In one embodiment, $R_3$ is hydrogen.

In another embodiment, $R_4$ is selected from hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_4$ is selected from halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_4$ is selected from hydrogen, alkoxy, halogen, cyano, alkylsulfonyl and nitro.

In one embodiment, $R_4$ is hydrogen.

In another embodiment, $R_5$ is selected from hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_5$ is selected from halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_5$ is selected from hydrogen, alkoxy, halogen, cyano, alkylsulfonyl and nitro.

In one embodiment, $R_5$ is hydrogen.

In another embodiment, $R_6$ is selected from hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_6$ is selected from halogen, $C_1$-$C_4$ alkyl, $C_3$-$C_6$ cycloalkyl, $C_1$-$C_4$ alkoxy, $C_3$-$C_6$ cycloalkyloxy, cyano and alkylsulfonyl.

In another embodiment, $R_6$ is selected from hydrogen, alkoxy, halogen, cyano, alkylsulfonyl and nitro.

In one embodiment, $R_6$ is hydrogen.

In one embodiment, $R_7$ is selected from hydrogen and $C_1$-$C_4$ alkyl.

In another embodiment, $R_7$ is $C_1$-$C_4$ alkyl.

In another embodiment, $R_7$ is hydrogen.

In one embodiment, $R_8$ is selected from hydrogen and $C_1$-$C_4$ alkyl.

In another embodiment, $R_8$ is $C_1$-$C_4$ alkyl.

In another embodiment, $R_8$ is hydrogen.

Compounds of the disclosure may contain asymmetric centers and exist as different enantiomers or diastereomers or a combination of these therein. All enantiomeric, diastereomeric forms of Formulas (I) and (II) are embodied herein.

Compound of the disclosure may exist as geometric isomers and tautomeric forms or a combination of these therein. When a compound of Formulas (I) or (II) contains an alkenyl or an imino group, geometric cis/trans (E/Z) isomers are possible. All cis/trans isomeric forms and tautomeric forms of Formulas (I) and (II) are embodied herein and are represented by the formula.

Compounds in the disclosure may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include lithium, sodium, potassium, magnesium, calcium and zinc. Salts derived from organic bases include ammonia, primary, secondary and tertiary amines, and amino acids. Salts derived from inorganic acids include sulfuric, hydrochloric, phosphoric, hydrobromic. Salts derived from organic acids include $C_{1-6}$ alkyl carboxylic acids, di-carboxylic acids and tricarboxylic acids such as acetic acid, proprionic acid, fumaric acid, maleic acid, succinic acid, tartaric acid, adipic acid and citric acid, and alkylsulfonic acids such as methanesulphonic, and aryl sulfonic acids such as para-tolouene sulfonic acid and benzene sulfonic acid.

Compounds in the disclosure may be in the form of a solvate. This occurs when a compound of Formulas (I) or (II) has an energetically favorable interaction with a solvent, crystallizes in a manner that it incorporates solvent molecules into the crystal lattice or a complex is formed with solvent molecules in the solid or liquid state. Examples of solvents forming solvates are water (hydrates), MeOH, EtOH, iPrOH, and acetone.

Compounds in the disclosure may exist in different crystal forms known as polymorphs. Polymorphism is the ability of a substance to exist in two or more crystalline phases that have different arrangements and/or conformations of the molecule in the crystal lattice.

Compounds in the disclosure may exist as isotopically labeled compounds of Formulas (I) or (II) where one or more atoms are replaced by atoms having the same atomic number but a different atomic mass from the atomic mass which is predominantly seen in nature. Examples of isotopes include, but are not limited to hydrogen isotopes (deuterium, tritium), carbon isotopes ($^{11}C$, $^{13}C$, $^{14}C$) and nitrogen isotopes ($^{13}N$, $^{15}N$). For example, substitution with heavier isotopes such as deuterium ($^2H$) may offer certain therapeutic advantages resulting from greater metabolic stability which could be preferable and lead to longer in vivo half-life or dose reduction in a mammal or human.

Prodrugs of compounds embodied by Formulas (I) or (II) are also within the scope of this disclosure. Particular derivatives of compounds of Formulas (I) or (II) which may have little to negligible pharmacological activity themselves, can, when administered to a mammal or human, be converted into compounds of Formulas (I) or (II) having the desired biological activity.

Compounds in the disclosure and their pharmaceutically acceptable salts, prodrugs, as well as metabolites of the compounds, may also be used to treat certain eating disorders, obesity, compulsive gambling, sexual disorders, narcolepsy, sleep disorders, diabetes, metabolic syndrome, neurodegenerative disorders and CNS disorders/conditions as well as in smoking cessation treatment.

In one embodiment the treatment of CNS disorders and conditions by the compounds of the disclosure can include Huntington's disease, schizophrenia and schizo-affective conditions, delusional disorders, drug-induced psychoses, panic and obsessive compulsive disorders, post-traumatic stress disorders, age-related cognitive decline, attention deficit/hyperactivity disorder, bipolar disorders, personality disorders of the paranoid type, personality disorders of the schizoid type, psychosis induced by alcohol, amphetamines, phencyclidine, opioids hallucinogens or other drug-induced psychosis, dyskinesia or choreiform conditions including dyskinesia induced by dopamine agonists, dopaminergic therapies, psychosis associated with Parkinson's disease, psychotic symptoms associated with other neurodegenerative disorders including Alzheimer's disease, dystonic conditions such as idiopathic dystonia, drug-induced dystonia, torsion dystonia, and tardive dyskinesia, mood disorders including major depressive episodes, post-stroke depression, minor depressive disorder, premenstrual dysphoric disorder, dementia including but not limited to multi-infarct dementia, AIDS-related dementia, and neurodegenerative dementia, In another embodiment, compounds of the disclosure may be used for the treatment of eating disorders, obesity, compulsive gambling, sexual disorders, narcolepsy, sleep disorders as well as in smoking cessation treatment.

In a further embodiment, compounds of the disclosure may be used for the treatment of obesity, schizophrenia, schizo-affective conditions, Huntington's disease, dystonic conditions and tardive dyskinesia.

In another embodiment, compounds of the disclosure may be used for the treatment of schizophrenia, schizo-affective conditions, Huntington's disease and obesity.

In a further embodiment, compounds of the disclosure may be used for the treatment of schizophrenia and schizo-affective conditions.

In an additional embodiment, compounds of the disclosure may be used for the treatment of Huntington's disease.

In another embodiment, compounds of the disclosure may be used for the treatment of obesity and metabolic syndrome.

Compounds of the disclosure may also be used in mammals and humans in conjunction with conventional antipsychotic medications including but not limited to Clozapine, Olanzapine, Risperidone, Ziprasidone, Haloperidol, Aripiprazole, Sertindole and Quetiapine. The combination of a compound of Formula (I) or (II) with a subtherapeutic dose of an aforementioned conventional antipsychotic medication may afford certain treatment advantages including improved side effect profiles and lower dosing requirements.

DEFINITIONS

Alkyl is meant to denote a linear or branched saturated or unsaturated aliphatic $C_1$-$C_8$ hydrocarbon which can be optionally substituted with up to 3 fluorine atoms. Unsaturation in the form of a double or triple carbon-carbon bond may be internal or terminally located and in the case of a double bond both cis and trans isomers are included. Examples of alkyl groups include but are not limited to methyl, trifluoromethyl, ethyl, trifluoroethyl, isobutyl, neopentyl, cis- and trans-2-butenyl, isobutenyl, propargyl. $C_1$-$C_4$ alkyl is the subset of alkyl limited to a total of up to 4 carbon atoms.

In each case in which a size range for the number of atoms in a ring or chain is disclosed, all subsets are disclosed. Thus, $C_x$-$C_y$ includes all subsets, e.g., $C_1$-$C_4$ includes $C_2$-$C_4$, $C_1$-$C_3$ etc.

Acyl is an alkyl-C(O)— group wherein alkyl is as defined above. Examples of acyl groups include acetyl and propionyl.

Alkoxy is an alkyl-O— group wherein alkyl is as defined above. $C_1$-$C_4$ alkoxy is the subset of alkyl-O— where the subset of alkyl is limited to a total of up to 4 carbon atoms. Examples of alkoxy groups include methoxy, trifluoromethoxy, ethoxy, trifluoroethoxy, and propoxy Alkoxyalkyl is an alkyl-O—($C_1$-$C_4$ alkyl)-group wherein alkyl is as defined above. Examples of alkoxyalkyl groups include methoxymethyl and ethoxymethyl.

Alkoxyalkyloxy is an alkoxy-alkyl-O— group wherein alkoxy and alkyl are as defined above. Examples of alkoxyalkyloxy groups include methoxymethyloxy ($CH_3OCH_2O$—) and methoxyethyloxy ($CH_3OCH_2CH_2O$—) groups.

Alkylthio is alkyl-S— group wherein alkyl is as defined above.

Alkylsulfonyl is alkyl-$SO_2$— wherein alkyl is as defined above.

Alkylamino is alkyl-NH— wherein alkyl is as defined above.

Dialkylamino is (alkyl)$_2$-N— wherein alkyl is as defined above.

Amido is $H_2NC(O)$—

Alkylamido is alkyl-NHC(O)— wherein alkyl is as defined above.

Dialkylamido is (alkyl)$_2$-NC(O)—wherein alkyl is as defined above.

Aromatic is heteroaryl or aryl wherein heteroaryl and aryl are as defined below.

Aryl is a phenyl or napthyl group. Aryl groups may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —OC(O)$R_a$, —OC(O)O$R_a$, —OC(O)NH$R_a$, —OC(O)N($R_a$), —S$R_a$, —S(O)$R_a$, —$NH_2$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)C(O)NH($R_b$), —N($R_a$)C(O)NH($R_b$)$_2$, —C(O)$NH_2$, —C(O)NH$R_a$, —C(O)N($R_a$)($R_b$), —$CO_2$H, —$CO_2R_a$, —COR$_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Arylalkyl is an aryl-alkyl-group wherein aryl and alkyl are as defined above.

Aryloxy is an aryl-O— group wherein aryl is as defined above.

Arylalkoxy is an aryl-($C_1$-$C_4$ alkyl)-O— group wherein aryl is as defined above.

Carboxy is a $CO_2H$ or $CO_2R_c$ group wherein $R_c$ is independently chosen from, alkyl, $C_1$-$C_4$ alkyl, cycloalkyl, arylalkyl, cycloalkylalkyl, $CF_3$, and alkoxyalkyl, wherein alkyl is as defined above and cycloalkyl is as defined below.

Cycloalkyl is a $C_3$-$C_7$ cyclic non-aromatic hydrocarbon which may contain a single double bond and is optionally and independently substituted with up to three groups selected from $C_1$-$C_4$alkyl, $C_1$-$C_4$alkoxy, hydroxyl and oxo. Examples of cycloalkyl groups include cyclopropyl, cyclobutyl, cyclopentyl, cyclohexyl, cyclopentenyl and cyclohexanoyl.

Cycloalkyloxy is a cycloalkyl-O— group wherein cycloalkyl is as defined above. Examples include cyclopropyloxy, cyclobutyloxy and cyclopentyloxy. $C_3$-$C_6$ cycloalkyloxy is the subset of cycloalkyl-O— where cycloalkyl contains 3-6 carbon atoms.

Cycloalkylalkyl is a cycloalkyl-($C_1$-$C_4$ alkyl)-group. Examples include cyclopropylmethyl, cyclopropylethyl, cyclohexylmethyl and cyclohexylethyl.

Cycloalkylalkoxy is a cycloalkyl-($C_1$-$C_4$ alkyl)-O— group wherein cycloalkyl and alkyl are as defined above. Examples of cycloalkylalkoxy groups include cyclopropylmethoxy, cyclopentylmethoxy and cyclohexylmethoxy.

Halogen is F, Cl, Br or I.

Heteroaryl is a tetrazole, 1,2,3,4-oxatriazole, 1,2,3,5-oxatriazole, a mono or bicyclic aromatic ring system, or a heterobicyclic ring system with one aromatic ring having 5 to 10 ring atoms independently selected from C, N, O and S, provided that not more than 3 ring atoms in any single ring are other than C. Examples of heteroaryl groups include but are not limited to thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, 1,3,4-triazolyl, pyrimidinyl, pyrazinyl, indolyl, quinolyl, tetrahydroquinolyl, isoquinolyl, tetrahydroisoquinolyl, indazolyl, benzthiadiazololyl, benzoxadiazolyl and benzimidazolyl. Heteroaryl groups may be optionally and independently substituted with up to 3 substituents independently selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —$OC(O)R_a$, —$OC(O)OR_a$, —$OC(O)NHR_a$, —$OC(O)N(R_a)$, —$S(O)R_a$, —$NH_2$, —$NHR_a$, —$N(R_a)(R_b)$, —$NHC(O)R_a$, —$N(R_a)C(O)R_b$, —$NHC(O)OR_a$, —$N(R_a)C(O)OR_b$, —$N(R_a)C(O)NH(R_b)$, —$N(R_a)C(O)NH(R_b)_2$, —$C(O)NH_2$, —$C(O)NHR_a$, —$C(O)N(R_a)(R_b)$, —$CO_2H$, —$CO_2R_a$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Heteroarylalkyl is a heteroaryl-($C_1$-$C_4$ alkyl)-group wherein heteroaryl and alkyl are as defined above. Examples of heteroarylalkyl groups include 4-pyridinylmethyl and 4-pyridinylethyl.

Heteroaryloxy is a heteroaryl-O group wherein heteroaryl is as defined above.

Heteroarylalkoxy is a heteroaryl-($C_1$-$C_4$ alkyl)-O— group wherein heteroaryl and alkoxy are as defined above.

Examples of heteroarylalkyl groups include 4-pyridinylmethoxy and 4-pyridinylethoxy.

Heterobicyclic ring system is a ring system having 8-10 atoms independently selected from C, N, O and S, provided that not more than 3 ring atoms in any single ring are other than carbon and provided that at least one of the rings is aromatic; said bicyclic ring may be optionally and independently substituted with up to 3 substituents independently selected from alkyl, alkoxy, cycloalkyl, $C_3$-$C_6$ cycloalkyloxy, cycloalkylalkyl, halogen, nitro, alkylsulfonyl and cyano. Examples of 8-10 membered heterobicyclic ring systems include but are not limited to 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl, tetrahydroquinoxalinyl, benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-c]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl, [1,2,4]triazolo[4,3-a]pyridinyl, benzo[b]thienyl, benzo[c][1,2,5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl, 3H-imidazo[4,5-c]pyridinyl, benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl.

Heterocycloalkyl is a non-aromatic, monocyclic or bicyclic saturated or partially unsaturated ring system comprising 5-10 ring atoms selected from C, N, O and S, provided that not more than 2 ring atoms in any single ring are other than C. In the case where the heterocycloalkyl group contains a nitrogen atom the nitrogen may be substituted with an alkyl, acyl, —C(O)O-alkyl, —C(O)NH(alkyl) or a —C(O)N(alkyl)$_2$ group. Heterocycloalkyl groups may be optionally and independently substituted with hydroxy, alkyl and alkoxy groups and may contain up to two oxo groups where said oxo groups are attached via a carbon atom. Heterocycloalkyl groups may be linked to the rest of the molecule via either carbon or nitrogen ring atoms. Examples of heterocycloalkyl groups include tetrahydrofuranyl, tetrahydrothienyl, tetrahydro-2H-pyran, tetrahydro-2H-thiopyranyl, pyrrolidinyl, pyrrolidonyl, succinimidyl, piperidinyl, piperazinyl, N-methylpiperazinyl, morpholinyl, morpholin-3-one, thiomorpholinyl, thiomorpholin-3-one, 2,5-diazabicyclo[2.2.2]octanyl, 2,5-diazabicyclo[2.2.1]heptanyl, octahydro-1H-pyrido[1,2-a]pyrazine, 3-thia-6-azabicyclo[3.1.1]heptane and 3-oxa-6-azabicyclo[3.1.1]heptanyl Heterocycloalkylalkyl is a heterocycloalkyl-($C_1$-$C_4$ alkyl)- group wherein heterocycloalkyl is as defined above.

Heterocycloalkyloxy is a heterocycloalkyl-O— group wherein heterocycloalkyl is as defined above.

Heterocycloalkylalkoxy is a heterocycloalkyl-($C_1$-$C_4$ alkyl)-O— group wherein heterocycloalkyl is as defined above.

Imino is a —N=C— group.

Oxo is a —C(O)— group.

Phenyl is a benzene ring which may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —OC(O)$R_a$, —OC(O)O$R_a$, —OC(O)NH$R_a$, —OC(O)N($R_a$), —S$R_a$, —S(O)$R_a$, —$NH_2$, —NH$R_a$, —N($R_a$)$R_b$), —NHC(O)$R_a$, —N($R_a$)C(O)$R_b$, —NHC(O)O$R_a$, —N($R_a$)C(O)O$R_b$, —N($R_a$)C(O)NH($R_b$), —N($R_a$)C(O)NH($R_b$)$_2$, —C(O)$NH_2$, —C(O)NH$R_a$, —C(O)N($R_a$)($R_b$), —$CO_2$H, —$CO_2R_a$, —COR$_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Restricted phenyl is a benzene ring which may be optionally and independently substituted with up to three groups selected from halogen, $CF_3$, CN, alkoxy, alkoxyalkyl, aryloxy, alkoxyalkyloxy, heterocycloalkyl, heterocycloalkyloxy, heteroaryl, heteroaryloxy, —$OCH_2CH_2OCH_3$, —OC(O)$R_a$, —OC(O)O$R_a$, —OC(O)N($R_a$), —N($R_a$)($R_b$), —NHC(O)$R_a$, —N($R_a$)C(O)$R_b$, —NHC(O)O$R_a$, —N($R_a$)C(O)O$R_b$, —C(O)N($R_a$)($R_b$), —COR$_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^i$Pr, $^t$Bu, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Abbreviations used in the following examples and preparations include:

Ac Acyl (Me—C(O)—)
AcN Acetonitrile
BINAP 2,2'-bis(diphenylphosphino)-1,1'-binaphthyl
Bn Benzyl
Celite® Diatomaceous earth
DBU 1,8-Diazabicyclo[5.4.0]undec-7-ene
DCC N,N', Dicyclohexylcarbodiimide
DCM Dichloromethane
DIEA Di-isopropylethyl amine
DIPEA Di-isopropylethyl amine
DMAP 4-Dimethylaminopyridine
DMF Dimethylformamide
DMP Dess Martin Periodinane
DMSO Dimethyl sulfoxide
Dppf 1,4-Bis(diphenylphosphino) ferrocene
EDC 1-(3-Dimethylaminopropyl)-3-ethylcarbodiimide Hydrochloride
$Et_3N$ Triethylamine
g gram(s)
h Hour(s)
hr Hour(s)
HATU 2-(7-Aza-1H-benzotriazole-1-yl)-1,1,3,3-tetramethyluronium hexafluorophosphate
HMDS Hexamethyldisilazide
HOBt 1-Hydroxybenzotriazole
HPLC High Pressure Liquid Chromatography
HRMS High resolution mass spectrometry
i.v. Intravenous
KHMDS Potassium Hexamethydisilazide
LDA Lithium Di-isopropylamide
m Multiplet
m—meta
MEM Methoxyethoxymethyl
MeOH Methyl Alcohol or Methanol
min Minute(s)
mmol millimoles
mmole millimoles
Ms Mesylate
MS Mass Spectrometry
MW Molecular Weight
NBS N-Bromosuccinamide
NIS N-Iodosuccinamide
NMR Nuclear Magnetic Resonance
NMM N-Methyl Morpholine
NMP N-Methyl-2-pyrrolidone
o ortho
o/n overnight
p para
PCC Pyridinium Chlorochromate
PEPPSI 1,3-Bis(2,6-diisopropylphenyl)imidazolidene)(3-chloropyridinyl) palladium(II) dichloride
$PhNTf_2$ 1,1,1-trifluoro-N-phenyl-N-(trifluoromethylsulfonyl)methanesulfonamide
POPd Dihydrogen dichlorobis(di-tert-butylphosphinito-kp) palladate (2-)
p.s.i. Pounds per square inch
PPA Polyphosphoric acid
PPAA 1-Propanephosphonic Acid Cyclic Anhydride
PTSA p-Toluenesulfonic acid
PyBOP® Benzotriazol-1-yl-oxytripyrrolidinophosphonium hexafluorophosphate
RT (or rt) room temperature (about 20-25° C.)
s Singlet
sat. Saturated
t Triplet TBAF Tetra-butyl ammonium fluoride
TEA Triethylamine
TFA Trifluoroacetic Acid
THF Tetrahydrofuran
TLC Thin layer chromatography
TMS Trimethylsilyl
Tf Triflate
Tof-MS Time of Flight Mass Spectrometry
Ts Tosylate
v/v volume/volume
wt/v weight/volume

DETAILED DESCRIPTION OF THE DISCLOSURE

The cyclopropyl compounds of Formulas (I) and (II) may be prepared from multi-step organic synthesis routes from aryl or heteroaryl aldehydes by one skilled in the art of organic synthesis using established organic synthesis procedures. The starting aryl aldehydes may be prepared from halobenzenes via. treatment with a lithium base and dimethylformamide. Alternatively, the aryl aldehydes may be prepared by oxidation of the corresponding methylpyridine or substituted toluene to the corresponding aldehyde.

Compounds of the disclosure of Formula (I) in which Y═H are as described previously and thus having general Formula)(XVI may be prepared generally as depicted in Scheme 1.

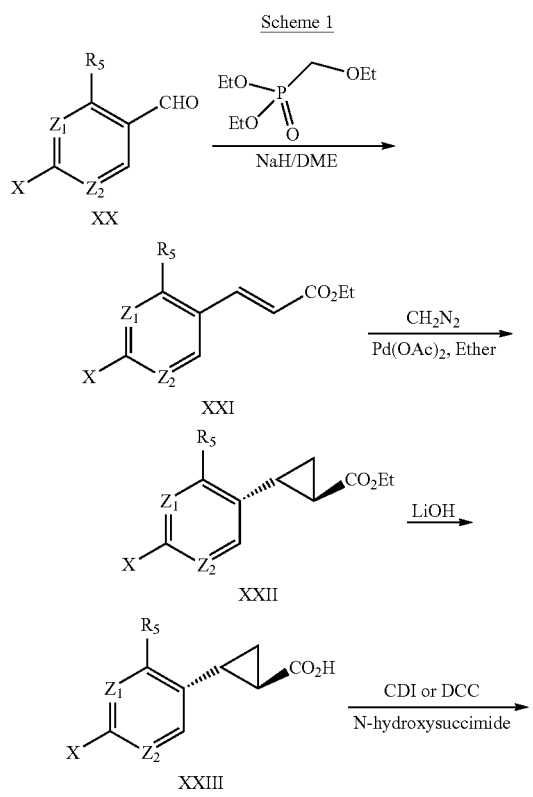

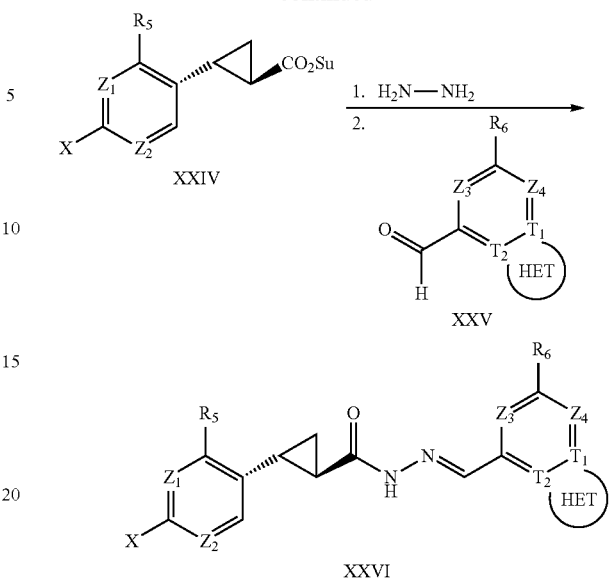

Compounds of the disclosure of Formula (II) in which Y═H are as described previously and thus having general Formula XXVIII may be prepared generally as depicted in Scheme 2.

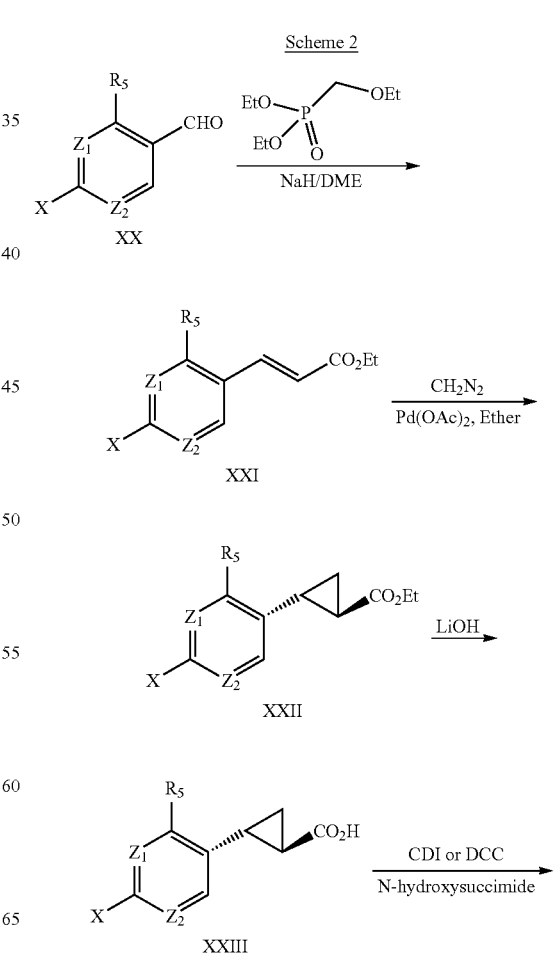

-continued

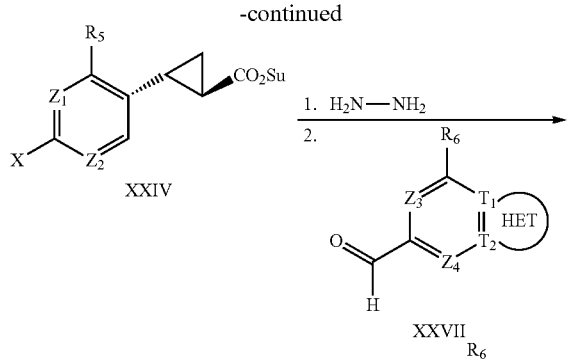

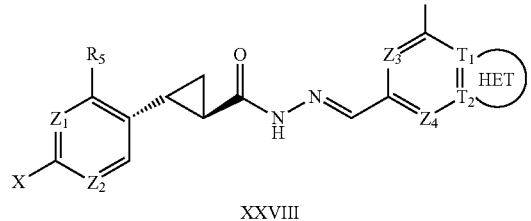

Reactive groups not involved in the above processes can be protected with standard protecting groups during the reactions and removed by standard procedures (T. W. Greene & P. G. M. Wuts, Protecting Groups in Organic Synthesis, Third Edition, Wiley-Interscience) known to those of ordinary skill in the art. Presently preferred protecting groups include methyl, benzyl, MEM, acetate and tetrahydropyranyl for the hydroxyl moiety, and BOC, Cbz, trifluoroacetamide and benzyl for the amino moiety, methyl, ethyl, tert-butyl and benzyl esters for the carboxylic acid moiety.

Experimental Procedures

HPLC Conditions
Condition-A:
Column: Hypersil BDS C8 250×4.6 mm, 5 um (SHCL06E001)
Mobile Phase AcN (A): 0.1% TFA in Water. (B).
Flow rate: 1.5 ml/min (Gradient)
Condition-B:
Column: Zobrax SB-C18 250×4.6 mm, 5 um
Mobile Phase AcN (A): 0.1% TFA in Water. (B).
Flow rate: 1.5 ml/min (Gradient)
Condition-C:
Column: Targa C-18 250×4.6 mm, 5 um
Mobile Phase AcN (A): 0.1% TFA in Water. (B).
Flow rate: 1.5 ml/min (Gradient)
Condition-D:
Column: Targa C18 250×4.6 mm, 5 um (SHCL-12)
Mobile Phase AcN (A): 5M Ammonium Acetate in Water. (B).
Flow rate: 1.0 ml/min (Gradient
Condition-E:
Column: Higgins-C18 250×4.6 mm, 5um
Mobile Phase AcN (A): 0.1% TFA in Water. (B).
Flow rate: 1.5 ml/min (Gradient)
Condition-F:
Column: Chiralpak AD
Mobile Phase: n-Hexane:Ethanol (50:50)
Flow rate: 0.6 ml/min (Gradient)
Condition-G:
Column: Venusil C8, 250×4.6 mm, 5um.
Mobile Phase AcN (A): 0.1% TFA in Water. (B).
Flow rate: 1.5 ml/min (Gradient)
Condition-H:
Column: Eclipse XDB-C18, 150×4.6 mm, 5um.
Mobile Phase: 0.1% TFA in Water. (A).ACN (B)
Flow rate: 1.5 ml/min (Gradient)
Condition-I:
Column: Acquity BEH-C18, (50×2.1 mm, 1.7 um.)
Mobile Phase AcN (B)
Flow rate: 0.5 ml/min (Gradient)
Condition-J:
Column: Zobrax C18, (150×4.6 mm, 5 um.)
Mobile Phase AcN (A): 0.1% TFA in Water. (B).
Flow rate: 1.0 ml/min (Gradient)

Synthesis of (E)-2-(4-tert-butylphenyl)-N'-(isoquinolin-5-ylmethylene) cyclopropanecarbohydrazide (Example 122)

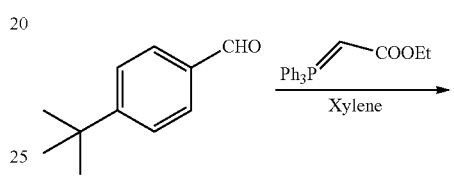

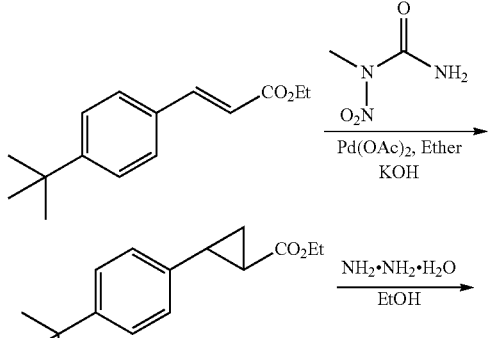

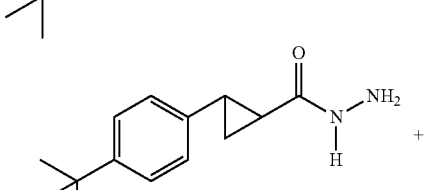

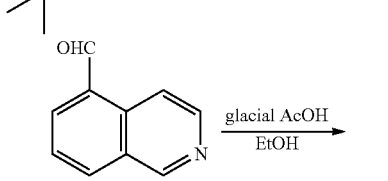

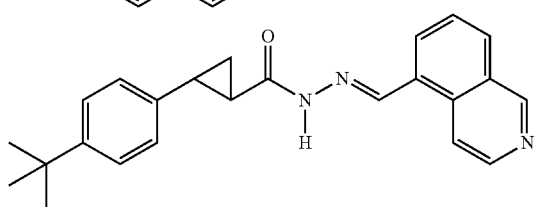

To a solution of 4-tert-butylbenzaldehyde (5 g, 0.03 mol) in xylenes (120 mL) was added the phosphine ylide (12.8 g, 0.036 mol) and the reaction mixture was then heated at 110° C. for 16 h. The reaction was concentrated in vacuo, and the residue diluted with water and extracted with ethyl acetate (2×100 mL). The combined organic layers were dried over magnesium sulfate, filtered and then concentrated in vacuo. The crude material was purified via silica gel column chromatography eluting with 5% ethyl acetate in hexanes to afford (E)-ethyl 3-(4-tert-butylphenyl)acrylate (5.5 g, 77%) as an oil.

To a −40° C. solution of (E)-ethyl 3-(4-tert-butylphenyl) acrylate (1.0 g, 4.3 mol) in ether (20 mL), freshly prepared diazomethane was added dropwise over 10 minutes. Pd(OAc)$_2$ (30 mg, 0.133 mol) was then added. The reaction mixture was stirred for another 10 min at −40° C., and then filtered through a pad of Celite® and precipitate washed with ether. The filtrate was concentrated in vacuo and the crude material was then purified via silica gel column chromatography to afford ethyl 2-(4-tert-butylphenyl)cyclopropanecarboxylate (0.9 g, 84%) as an oil.

To a room temperature solution of ethyl 2-(4-tert-butylphenyl)cyclopropanecarboxylate (1.0 g, 0.004 mol) in ethanol (10 mL) was added hydrazine hydrate (2 g, 0.04 mol) and the reaction mixture was then heated at 95° C. for 16 h. The mixture was then concentrated in vacuo and the solid that was obtained was washed with hexanes to afford 2-(4-tert-butylphenyl)cyclopropanecarbohydrazide (0.78 g, 82%) as a white solid.

To a room temperature solution of 2-(4-tert-butylphenyl) cyclopropanecarbohydrazide (200 mg, 0.86 mmol) in ethanol (10 mL) were added isoquinoline-5-carbaldehyde (162 mg, 1.0 mmol) and a catalytic amount of glacial AcOH (0.4 mL) under an inert atmosphere. The reaction mixture was then stirred at 90° C. for 4 h, concentrated in vacuo, and the residue was then dissolved in DCM (50 mL). The organic layer was washed with saturated NaHCO$_3$ solution (15 mL) and brine (15 mL). The organic layer was then separated, dried over anhydrous Na$_2$SO$_4$, filtered and evaporated in vacuo to obtain the crude product. The crude material was purified via silica gel column chromatography eluting with 1% MeOH in dichloromethane to afford (E)-2-(4-tert-butylphenyl)-N'-(isoquinolin-5-ylmethylene) cyclopropanecarbohydrazide (160 mg, 50%) as a white solid. $^1$H NMR (500 MHz, d$_6$-DMSO): δ 11.60 (s, 1H), 9.38 (s, 1H), 8.71-8.56 (m, 2H), 8.25-8.12 (m, 2H), 8.11-7.99 (m, 2H), 7.39-7.29 (m, 2H), 7.19-7.06 (m, 2H), 2.41-2.33 (m, 1H), 1.95-1.90 (m, 1H), 1.42-1.34 (m, 2H), 1.25 (s, 9H). MS: M m/z=372.2 HPLC: 96%, (Condition-A).

Synthesis of (E)-2-(4-tert-butylphenyl)-N'-(isoquinolin-5-ylmethylene) cyclopropanecarbohydrazide (Example 195)

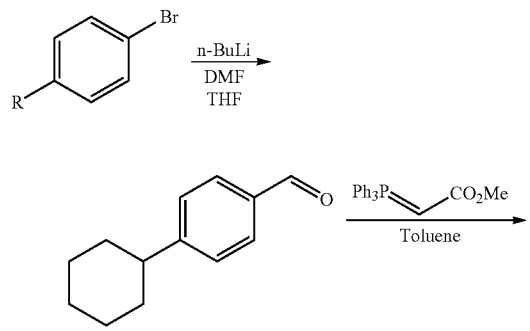

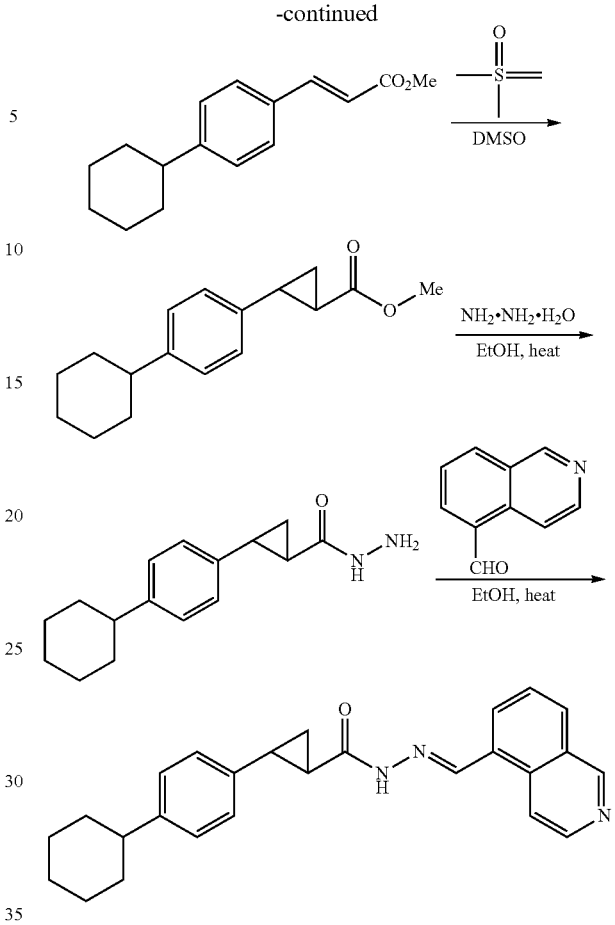

To a solution of 1-bromo-4-cyclohexylbenzene (850 mg, 3.55 mmol) in THF (4.0 mL) was added n-BuLi (3.1 mL, 4.62 mmol) at −78° C. under an inert atmosphere. The reaction mixture was stirred for 60 min at −78° C., and then DMF (2.8 mL) was added. The reaction mixture was then stirred for an additional hour at −78° C., warmed to 0° C., and quenched with a saturated NH$_4$Cl solution. The mixture was then extracted with ethyl acetate (2×30 mL). The combined organic layers were then dried over magnesium sulfate, filtered and concentrated in vacuo to obtain the crude product. The crude material was purified via silica gel column chromatography to afford 4-cyclohexylbenzaldehyde (250 mg, 38%) as a solid.

To a room temperature solution of 4-cyclohexylbenzaldehyde (250 mg, 1.32 mmol) in toluene (45 mL) was added phosphine ylide (535 mg, 1.59 mmol) under an inert atmosphere. The reaction mixture was then heated at 100° C. for 16 h, cooled to RT, diluted with n-hexane, stirred for 10 minutes and the precipitate was filtered. The filtrate was concentrated in vacuo, and the crude material was purified via silica gel column chromatography to afford (E)-methyl 3-(4-cyclohexylphenyl)acrylate (200 mg, 62%) as a solid.

To a solution of (E)-methyl 3-(4-cyclohexylphenyl)acrylate (200 mg, 0.82 mmol) in DMSO (20 mL) was added freshly prepared Corey's reagent (92 mg, 0.98 mmol) at RT and stirred for 3 h. The reaction was quenched with cold water and then extracted with EtOAc (2×20 mL). The combined organic layers were dried over magnesium sulfate, filtered and then concentrated in vacuo to obtain crude product. The crude material was purified via silica gel column chromatography eluting with 5% EtOAc/95% hexanes to afford methyl 2-(4-cyclohexylphenyl)cyclopropanecarboxylate (150 mg, 47%) as a solid.

To a room temperature solution of methyl 2-(4-cyclohexylphenyl)cyclopropanecarboxylate (150 mg, 0.58 mmol) in ethanol (40 mL) was added hydrazine hydrate (293 mg, 5.85 mmol). The reaction mixture was then heated at 80° C. for 16 h, concentrated in vacuo and the residue dissolved in DCM (50 mL). The organic layer was washed with water, dried over magnesium sulfate, filtered and concentrated in vacuo to afford 2-(4-cyclohexylphenyl)cyclopropanecarbohydrazide (200 mg) which was taken on to the next step without further purification.

To a room temperature solution of 2-(4-cyclohexylphenyl)cyclopropanecarbohydrazide (200 mg) in ethanol (20 mL), was added isoquinoline-5-carbaldehyde (122 mg, 0.77 mmol) and acetic acid (0.5 mL). The reaction mixture was then heated at 80° C. for 3 h, concentrated in vacuo and the residue diluted with water and extracted with EtOAc (2×20 mL). The layers were separated and then the combined organic layers were washed with a saturated NaHCO$_3$ solution, dried over magnesium sulfate, filtered and concentrated in vacuo to obtain the crude product. The crude material was purified via column chromatography eluting with 2% MeOH in dichloromethane to afford (E)-2-(4-cyclohexylphenyl)-N'-(isoquinolin-5-ylmethylene)cyclopropanecarbohydrazide (100 mg, 33%) as a white solid.

$^1$H NMR (500 MHz, CDCl$_3$): δ 9.30-9.22 (m, 1 H), 8.78-8.69 (m, 1 H), 8.58-8.49 (m, 1 H), 8.36-8.28 (m, 1 H), 8.18-8.09 (m, 1 H), 7.78-7.69 (m, 2 H), 7.18-7.10 (m, 5 H), 2.98-2.92 (m, 1 H), 2.56-2.48 (m, 2 H), 1.86-1.75 (m, 6 H), 1.45-1.36 (m, 4 H);

MS: M$^+$H: m/z=398.3; and HPLC: 99%, (Condition-C).

Synthesis of (E)-2-(biphenyl-4-yl)-N'-(isoquinolin-5-ylmethylene)cyclopropanecarbohydrazide (Example 196)

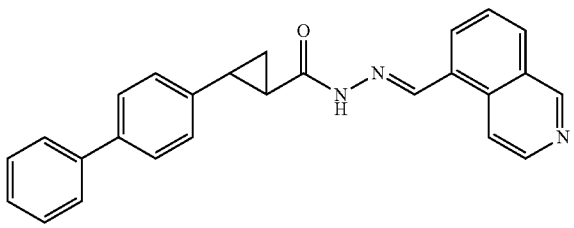 [SMILES: O=C(N/N=C/c1cccc2cnccc12)C1CC1c1ccc(-c2ccccc2)cc1]

Following the procedure for the preparation of (E)-2-(4-tert-butylphenyl)-N'-(isoquinolin-5-ylmethylene) cyclopropanecarbohydrazide provided the title compound (E)-2-(biphenyl-4-yl)-N'-(isoquinolin-5-ylmethylene) cyclopropanecarbohydrazide gave the title compound: Yield: 35%. $^1$H NMR (500 MHz, CD$_3$OD): δ 9.38-9.20 (m, 1 H), 8.81-8.71 (m, 1 H), 8.60-8.58 (m, 1 H), 8.38-8.19 (m, 2 H), 7.82-7.64 (m, 1 H), 7.63-7.54 (m, 5 H), 7.51-7.48 (m, 2 H), 7.39-7.24 (m, 3 H), 3.16-3.08 (m, 1 H), 2.08-2.04 (m, 1 H), 1.59-1.50 (m, 2 H). MS: M$^+$H: m/z=392.1 HPLC: 97%, (Condition-B).

Synthesis of (E)-2-(4-tert-butylphenyl)-N'-(1-(isoquinolin-5-yl)ethylidene)cyclopropanecarbohydrazide (Example 197)

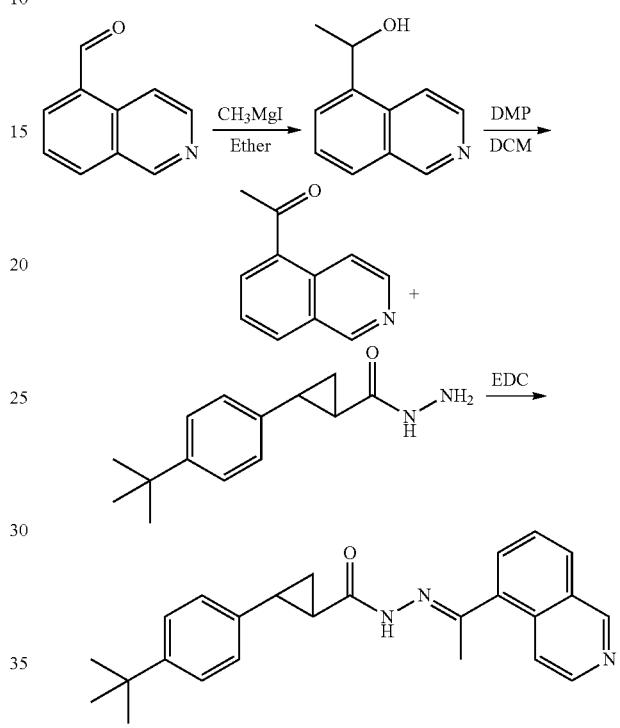

To a mixture of Mg turnings (0.2 g, 7.9 mmol) in ether (10 mL) was added MeI (1.13 g, 7.9 mmol) slowly at RT under an inert atmosphere. After being stirred for 1 h at RT, the reaction mixture was cooled to −10° C. and a solution of isoquinoline-5-carbaldehyde (0.5 g, 3.18 mmol) in ether (10 mL) was added. The reaction mixture was then stirred for an additional hour at RT, quenched with saturated NH$_4$Cl solution and extracted with EtOAc (3×50 mL). The combined organic layers were washed with water and brine, dried over Na$_2$SO$_4$, filtered and concentrated in vacuo to obtain the crude product. The crude material was purified via silica gel column chromatography using 30% ethyl acetate in hexanes to afford 1-(isoquinolin-5-yl)ethanol (0.53 g, 97%) as an off-white solid.

To a 10° C. solution of 1-(isoquinolin-5-yl)ethanol (530 mg, 3.0 mmol) in DCM (10 mL) was added Dess-Martin periodinane (1.9 g, 4.0 mmol) under a N$_2$ atmosphere. The reaction mixture was stirred for 16 h at room temperature and then quenched with saturated NaHCO$_3$ solution (5 mL). The organic layer was separated, washed with water and brine, dried over anhydrous Na$_2$SO$_4$, filtered and concentrated in vacuo to obtain the crude product. The crude material was purified via silica gel column chromatography using 20% ethyl acetate in hexanes to afford 1-(isoquinolin-5-yl)ethanone (500 mg, 95.4%) as an off-white solid.

A solution of 2-(4-tert-butylphenyl)cyclopropanecarbohydrazide (200 mg, 0.86 mmol) and 1-(isoquinolin-5-yl)ethanone (147 mg, 0.86 mmol) in 1,2-dichloroethane (10 mL) was stirred at room temperature for 2 h. The reaction mixture was then diluted with water (5 mL) and the organic layer was separated, washed brine, dried over anhydrous Na₂SO₄, filtered and concentrated in vacuo. The crude material was purified via silica gel column chromatography to afford (E)-2-(4-tert-butylphenyl)-N'-(1-(isoquinolin-5-yl)ethylidene)cyclopropanecarbohydrazide (150 mg, 45%) as an off-white solid.

$^{1}$H NMR (500 MHz, CDCl$_3$): δ 9.23 (s, 1 H), 8.78 (s, 1 H), 8.26-8.20 (m, 1 H), 8.08-7.94 (m, 2 H), 7.79-7.72 (m, 1 H), 7.63-7.57 (m, 1 H), 7.38-7.22 (m, 2 H), 7.08 6.98 (m, 2 H), 2.98-2.90 (m, 1 H), 2.38 (s, 3 H), 2.67-2.61 (m, 1 H), 1.91-1.86 (m, 2 H), 1.25 (s, 9 H). MS: M⁺H: m/z=386.2 and HPLC: 90%, (Condition-G).

Synthesis of (E)-2-(4-tert-butylphenyl)-N'-(isoquinolin-5-ylmethylene)-N-methylcyclopropanecarbohydrazide (Example 198)

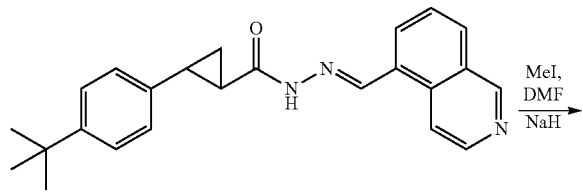

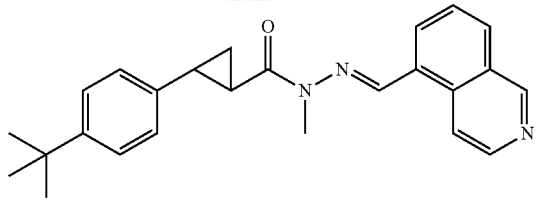

To a 0° C. suspension of NaH (16 mg, 0.6 mmol) in DMF (1 mL), (E)-2-(4-tert-butylphenyl)-N'-(isoquinolin-5-ylmethylene)cyclopropanecarbohydrazide (200 mg, 0.53 mmol) was added portionwise under nitrogen atmosphere. After being stirred for 1 h at 0° C., MeI (0.15 g, 1.0 mmol) was added and the reaction mixture stirred at RT for 1 h. The reaction mixture was then quenched with ice water and stirred for an additional 10 minutes. The precipitated solid was filtered and dried in vacuo to obtain the crude product. The crude material was purified via silica gel column chromatography using 20% ethyl acetate in hexanes to afford (E)-2-(4-tert-butylphenyl)-N'-(isoquinolin-5-ylmethylene)-N-methylcyclopropanecarbohydrazide (30 mg, 50%) as an off-white solid. $^{1}$H NMR (500 MHz, CDCl$_3$): δ 9.24 (bs, 1 H), 8.50-8.41 (m, 1 H), 8.26-8.20 (m, 1 H), 8.02-7.94 (m, 2 H), 7.66-7.58 (m, 2 H), 7.39 (d, J=7.2 Hz, 2 H), 7.14 (d, J=7.2 Hz, 2 H), 3.28 (s, 3 H), 3.39-3.12 (m, 1 H), 2.63-2.56 (m, 1 H), 1.84-1.78 (m, 1 H), 1.49-1.38 (m, 1 H), 1.37 (s, 9 H). MS: M⁺H: m/z=386.2 and HPLC: 91%, (Condition-G).

Tables

In a further aspect the compounds of the disclosure are embodied in with distinct examples listed in the table below taken from Formula (I):

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 100 | imidazole (T₁=N, T₂=NH) | Ph | | CH | CH | CH | CH | CH | H | H | H | H |
| 101 | thiazole (T₁=N, T₂=S) | Ph | | CH | CH | CH | CH | CH | H | H | H | H |
| 102 | oxazole (T₁=N, T₂=O) | Ph | | CH | CH | CH | CH | CH | H | H | H | H |
| 103 | pyridine (T₁=N, T₂=CH) | Ph | | CH | CH | CH | CH | CH | H | H | H | H |

-continued

| Ex | HET | X | Y | Z₁ | Z₂ | Z₃ | Z₄ | R₅ | R₆ | R₇ | R₈ |
|----|-----|---|---|----|----|----|----|----|----|----|----|
| 104 | (T₁=N, T₂=CH pyrimidine-like) | Ph | CH | CH | CH | CH | CH | H | H | H | H |
| 105 | (T₁=CH, T₂=CH, N at meta) | Ph | CH | CH | CH | CH | CH | H | H | H | H |
| 106 | (T₁=CH, T₂=C–N) | Ph | CH | CH | CH | CH | CH | H | H | H | H |
| 107 | (T₁–NH, T₂=CH dihydro) | Ph | CH | CH | CH | CH | CH | H | H | H | H |
| 108 | (T₁=CH, T₂–CH₂–NH) | Ph | CH | CH | CH | CH | CH | H | H | H | H |
| 109 | (T₁=CH, T₂–CH₂–NH inverted) | Ph | CH | CH | CH | CH | CH | H | H | H | H |
| 110 | (T₁=CH, T₂–NH tetrahydro) | Ph | CH | CH | CH | CH | CH | H | H | H | H |
| 111 | (T₁–N(CH₃), T₂=CH) | Ph | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 112 | | Ph | CH | CH | CH | CH | CH | H | H | H | H |
| 113 | | Ph | CH | CH | CH | CH | CH | H | H | H | H |
| 114 | | Ph | CH | CH | CH | CH | CH | H | H | H | H |
| 115 | | Ph | CH | CH | CH | CH | CH | H | H | H | H |
| 116 | | Ph | CH | CH | CH | CH | CH | H | H | H | H |
| 117 | | Ph | CH | CH | CH | CH | CH | H | H | H | H |
| 118 | | $^t$Bu | CH | CH | CH | CH | CH | H | H | H | H |
| 119 | | $^t$Bu | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 120 | (T1=N, T2–O oxazole) | ᵗBu | CH | CH | CH | CH | CH | H | H | H | H |
| 121 | (pyridine, N adjacent to T1) | ᵗBu | CH | CH | CH | CH | CH | H | H | H | H |
| 122 | (pyridine, N adjacent to T1 other side) | ᵗBu | CH | CH | CH | CH | CH | H | H | H | H |
| 123 | (pyridine, N adjacent to T2) | ᵗBu | CH | CH | CH | CH | CH | H | H | H | H |
| 124 | (pyridazine) | ᵗBu | CH | CH | CH | CH | CH | H | H | H | H |
| 125 | (tetrahydro, NH adjacent to T1) | ᵗBu | CH | CH | CH | CH | CH | H | H | H | H |
| 126 | (tetrahydro, NH adjacent to T2) | ᵗBu | CH | CH | CH | CH | CH | H | H | H | H |
| 127 | (tetrahydro, NH at other position) | ᵗBu | CH | CH | CH | CH | CH | H | H | H | H |

| Ex | HET | X | Y | Z₁ | Z₂ | Z₃ | Z₄ | R₅ | R₆ | R₇ | R₈ |
|---|---|---|---|---|---|---|---|---|---|---|---|
| 128 | (tetrahydropyridazine, NH) | ᵗBu | CH | CH | CH | CH | CH | H | H | H | H |
| 129 | (tetrahydropyridazine, N-Me at T₁ side) | ᵗBu | CH | CH | CH | CH | CH | H | H | H | H |
| 130 | (tetrahydropyridine, N-Me) | ᵗBu | CH | CH | CH | CH | CH | H | H | H | H |
| 131 | (tetrahydropyridine, N-Me) | ᵗBu | CH | CH | CH | CH | CH | H | H | H | H |
| 132 | (tetrahydropyridazine, N-Me) | ᵗBu | CH | CH | CH | CH | CH | H | H | H | H |
| 133 | (pyrazole, NH) | ᵗBu | CH | CH | CH | CH | CH | H | H | H | H |
| 134 | (pyrazole, N-Me) | ᵗBu | CH | CH | CH | CH | CH | H | H | H | H |
| 135 | (triazole, N-Me) | ᵗBu | CH | CH | CH | CH | CH | H | H | H | H |

-continued
| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 136 | 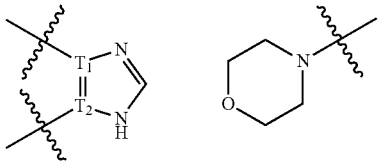 | 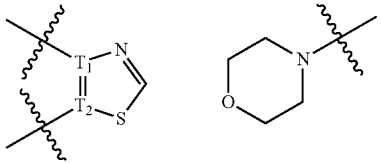 | CH | CH | CH | CH | CH | H | H | H | H |
| 137 | 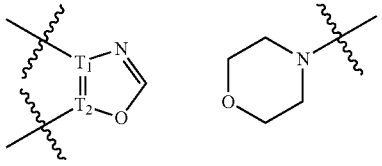 | 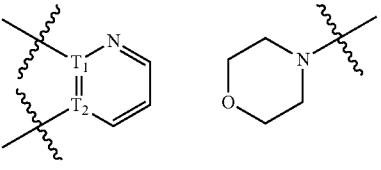 | CH | CH | CH | CH | CH | H | H | H | H |
| 138 | 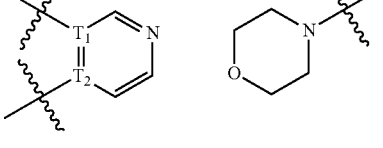 | 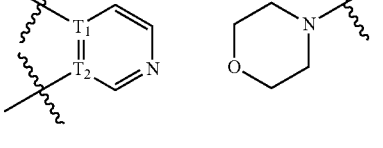 | CH | CH | CH | CH | CH | H | H | H | H |
| 139 | 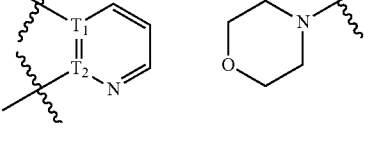 | 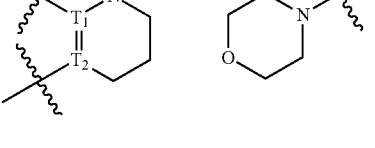 | CH | CH | CH | CH | CH | H | H | H | H |
| 140 | | | CH | CH | CH | CH | CH | H | H | H | H |
| 141 | | | CH | CH | CH | CH | CH | H | H | H | H |
| 142 | | | CH | CH | CH | CH | CH | H | H | H | H |
| 143 | | | CH | CH | CH | CH | CH | H | H | H | H |

-continued
| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 144 | 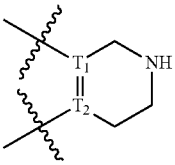 | 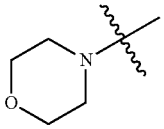 | CH | CH | CH | CH | CH | H | H | H | H |
| 145 | 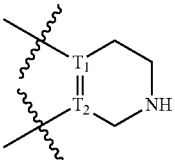 | 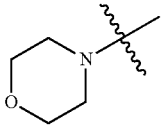 | CH | CH | CH | CH | CH | H | H | H | H |
| 146 | 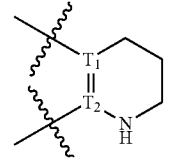 | 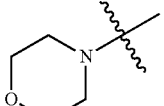 | CH | CH | CH | CH | CH | H | H | H | H |
| 147 | 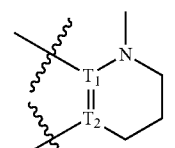 | 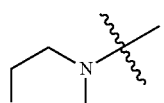 | CH | CH | CH | CH | CH | H | H | H | H |
| 148 | 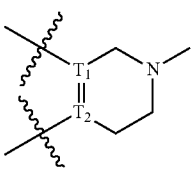 | 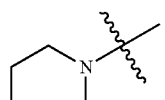 | CH | CH | CH | CH | CH | H | H | H | H |
| 149 | 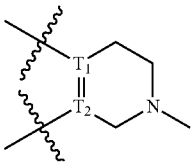 | 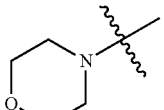 | CH | CH | CH | CH | CH | H | H | H | H |
| 150 | 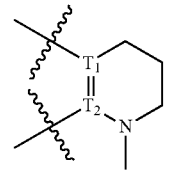 | 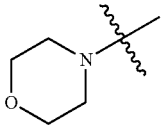 | CH | CH | CH | CH | CH | H | H | H | H |
| 151 | 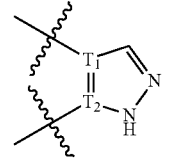 | 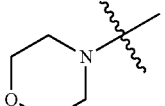 | CH | CH | CH | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 152 | triazole (T₁=CH, T₂=N, N-Me) | morpholine | CH | CH | CH | CH | CH | H | H | H | H |
| 153 | triazole (T₁=CH, T₂=N, N-Me) | morpholine | CH | CH | CH | CH | CH | H | H | H | H |
| 154 | pyridine | 4-F-phenyl | CH | CH | CH | CH | CH | H | H | H | H |
| 155 | pyridine | 4-Cl-phenyl | CH | CH | CH | CH | CH | H | H | H | H |
| 156 | pyridine | 4-CN-phenyl | CH | CH | CH | CH | CH | H | H | H | H |
| 157 | pyridine | 4-MeO-phenyl | CH | CH | CH | CH | CH | H | H | H | H |
| 158 | pyridine | 4-F₃CO-phenyl | CH | CH | CH | CH | CH | H | H | H | H |
| 159 | pyridine | 4-methylpiperazine | CH | CH | CH | CH | CH | H | H | H | H |

-continued
| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 160 | 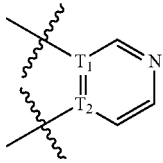 | 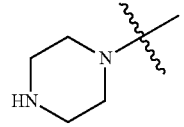 [SMILES: *N1CCNCC1] | CH | CH | CH | CH | CH | H | H | H | H |
| 161 | 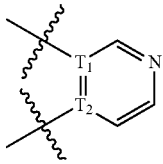 | 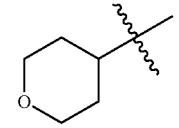 [SMILES: *C1CCOCC1] | CH | CH | CH | CH | CH | H | H | H | H |
| 162 | 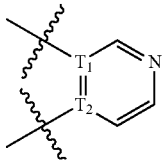 | 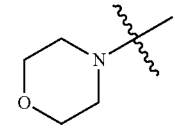 | N | CH | CH | CH | CH | H | H | H | H |
| 163 | 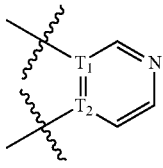 | 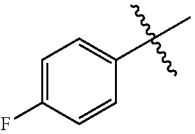 [SMILES: *c1ccc(F)cc1] | N | CH | CH | CH | CH | H | H | H | H |
| 164 | 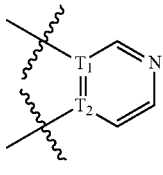 | 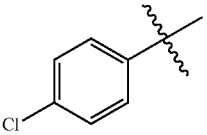 | N | CH | CH | CH | CH | H | H | H | H |
| 165 | 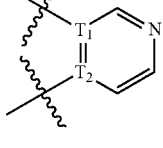 | 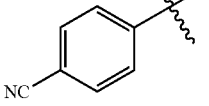 | N | CH | CH | CH | CH | H | H | H | H |
| 166 | 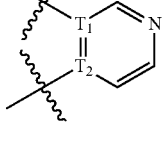 | 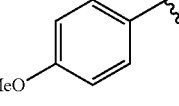 | N | CH | CH | CH | CH | H | H | H | H |
| 167 | 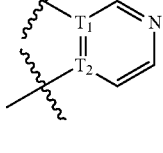 | 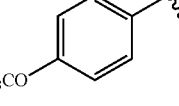 | N | CH | CH | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 168 | T₁=N, T₂=CH pyridine | N-methylpiperazine | N | CH | CH | CH | CH | H | H | H | H |
| 169 | T₁=N, T₂=CH pyridine | piperazine (HN) | N | CH | CH | CH | CH | H | H | H | H |
| 170 | T₁=N, T₂=CH pyridine | tetrahydropyran-4-yl | N | CH | CH | CH | CH | H | H | H | H |
| 171 | T₁=N, T₂=CH pyridine | ᵗBu | N | CH | CH | CH | CH | H | H | H | H |
| 172 | T₁=N, T₂=CH pyridine | Ph | N | CH | CH | CH | CH | H | H | H | H |
| 173 | T₁=N, T₂=CH pyridine | morpholino | CH | CH | N | CH | CH | H | H | H | H |
| 174 | T₁=N, T₂=CH pyridine | 4-F-phenyl | CH | CH | N | CH | CH | H | H | H | H |
| 175 | T₁=N, T₂=CH pyridine | 4-Cl-phenyl | CH | CH | N | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 176 | T1=N, T2 (pyridine) | 4-CN-phenyl | CH | CH | N | CH | CH | H | H | H | H |
| 177 | T1=N, T2 (pyridine) | 4-MeO-phenyl | CH | CH | N | CH | CH | H | H | H | H |
| 178 | T1=N, T2 (pyridine) | 4-F₃CO-phenyl | CH | CH | N | CH | CH | H | H | H | H |
| 179 | T1=N, T2 (pyridine) | 4-methylpiperazin-1-yl | CH | CH | N | CH | CH | H | H | H | H |
| 180 | T1=N, T2 (pyridine) | piperazin-1-yl | CH | CH | N | CH | CH | H | H | H | H |
| 181 | T1=N, T2 (pyridine) | tetrahydropyran-4-yl | CH | CH | N | CH | CH | H | H | H | H |
| 182 | T1=N, T2 (pyridine) | ᵗBu | CH | CH | N | CH | CH | H | H | H | H |
| 183 | T1=N, T2 (pyridine) | Ph | CH | CH | N | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 184 | T₁=N, T₂ (pyridine) | morpholin-4-yl | CH | CH | CH | N | CH | H | H | H | H |
| 185 | T₁=N, T₂ (pyridine) | 4-fluorophenyl | CH | CH | CH | N | CH | H | H | H | H |
| 186 | T₁=N, T₂ (pyridine) | 4-chlorophenyl | CH | CH | CH | N | CH | H | H | H | H |
| 187 | T₁=N, T₂ (pyridine) | 4-cyanophenyl | CH | CH | CH | N | CH | H | H | H | H |
| 188 | T₁=N, T₂ (pyridine) | 4-methoxyphenyl | CH | CH | CH | N | CH | H | H | H | H |
| 189 | T₁=N, T₂ (pyridine) | 4-(trifluoromethoxy)phenyl | CH | CH | CH | N | CH | H | H | H | H |
| 190 | T₁=N, T₂ (pyridine) | 4-methylpiperazin-1-yl | CH | CH | CH | N | CH | H | H | H | H |
| 191 | T₁=N, T₂ (pyridine) | piperazin-1-yl | CH | CH | CH | N | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 192 | T₁=N pyridine (T₂) | tetrahydropyran-4-yl | CH | CH | CH | N | CH | H | H | H | H |
| 193 | T₁=N pyridine (T₂) | ᵗBu | CH | CH | CH | N | CH | H | H | H | H |
| 194 | T₁=N pyridine (T₂) | Ph | CH | CH | CH | N | CH | H | H | H | H |
| 195 | T₁=N pyridine (T₂) | cyclohexyl | CH | CH | CH | CH | CH | H | H | H | H |
| 196 | T₁=N pyridine (T₂) | phenyl | CH | CH | CH | CH | CH | H | H | H | H |
| 197 | T₁=N pyridine (T₂) | ᵗBu | CH | CH | CH | CH | CH | H | H | H | Me |
| 198 | T₁=N pyridine (T₂) | ᵗBu | CH | CH | CH | CH | CH | H | H | Me | H |

In a further aspect the compounds of the disclosure are embodied in with distinct examples listed in the table below taken from Formula (II):

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 199 | imidazole | Ph | CH | CH | CH | CH | CH | H | H | H | H |
| 200 | thiazole | Ph | CH | CH | CH | CH | CH | H | H | H | H |
| 201 | oxazole | Ph | CH | CH | CH | CH | CH | H | H | H | H |
| 202 | pyridine | Ph | CH | CH | CH | CH | CH | H | H | H | H |
| 203 | pyridine | Ph | CH | CH | CH | CH | CH | H | H | H | H |
| 204 | pyridine | Ph | CH | CH | CH | CH | CH | H | H | H | H |
| 205 | pyridazine | Ph | CH | CH | CH | CH | CH | H | H | H | H |
| 206 | tetrahydropyrimidine | Ph | CH | CH | CH | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 207 | (T₁=T₂, T₁-CH₂-CH₂-NH-CH₂ ring) | Ph | CH | CH | CH | CH | CH | H | H | H | H |
| 208 | (T₁=T₂, piperidine NH variant) | Ph | CH | CH | CH | CH | CH | H | H | H | H |
| 209 | (T₁=T₂, piperidine with NH adjacent to T₂) | Ph | CH | CH | CH | CH | CH | H | H | H | H |
| 210 | (T₁=T₂, N-Me piperidine) | Ph | CH | CH | CH | CH | CH | H | H | H | H |
| 211 | (T₁=T₂, N-Me piperidine variant) | Ph | CH | CH | CH | CH | CH | H | H | H | H |
| 212 | (T₁=T₂, N-Me piperidine variant) | Ph | CH | CH | CH | CH | CH | H | H | H | H |
| 213 | (T₁=T₂, N-Me piperidine variant) | Ph | CH | CH | CH | CH | CH | H | H | H | H |
| 214 | (T₁=T₂, pyrazole NH) | Ph | CH | CH | CH | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 215 | (T₁=T₂, pyrazole N-Me) | Ph | CH | CH | CH | CH | CH | H | H | H | H |
| 216 | (T₁=T₂, pyrazole N-Me isomer) | Ph | CH | CH | CH | CH | CH | H | H | H | H |
| 217 | (T₁=T₂, triazole NH) | $^t$Bu | CH | CH | CH | CH | CH | H | H | H | H |
| 218 | (T₁=T₂, thiazole) | $^t$Bu | CH | CH | CH | CH | CH | H | H | H | H |
| 219 | (T₁=T₂, oxazole) | $^t$Bu | CH | CH | CH | CH | CH | H | H | H | H |
| 220 | (T₁=T₂, pyridine) | $^t$Bu | CH | CH | CH | CH | CH | H | H | H | H |
| 221 | (T₁=T₂, pyridine isomer) | $^t$Bu | CH | CH | CH | CH | CH | H | H | H | H |
| 222 | (T₁=T₂, pyridazine) | $^t$Bu | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 223 | (pyridazine fused) | $^tBu$ | CH | CH | CH | CH | CH | H | H | H | H |
| 224 | (dihydropyridine with NH) | $^tBu$ | CH | CH | CH | CH | CH | H | H | H | H |
| 225 | (tetrahydropyridine with NH top) | $^tBu$ | CH | CH | CH | CH | CH | H | H | H | H |
| 226 | (tetrahydropyridine with NH bottom) | $^tBu$ | CH | CH | CH | CH | CH | H | H | H | H |
| 227 | (dihydropyrazine with NH) | $^tBu$ | CH | CH | CH | CH | CH | H | H | H | H |
| 228 | (tetrahydropyridine with N-Me top) | $^tBu$ | CH | CH | CH | CH | CH | H | H | H | H |
| 229 | (tetrahydropyridine with N-Me bottom) | $^tBu$ | CH | CH | CH | CH | CH | H | H | H | H |
| 230 | (tetrahydropyrazine with N-Me) | $^tBu$ | CH | CH | CH | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 231 | (T₁-T₂-N-CH₂CH₂CH₂ ring, N-methyl) | tBu | CH | CH | CH | CH | CH | H | H | H | H |
| 232 | (T₁=T₂ fused pyrazole, NH) | tBu | CH | CH | CH | CH | CH | H | H | H | H |
| 233 | (T₁=T₂ pyrazole, N-methyl) | tBu | CH | CH | CH | CH | CH | H | H | H | H |
| 234 | (T₁=T₂ triazole, N-methyl) | tBu | CH | CH | CH | CH | CH | H | H | H | H |
| 235 | (T₁=T₂ imidazole, NH) | morpholine | CH | CH | CH | CH | CH | H | H | H | H |
| 236 | (T₁=T₂ thiazole, S) | morpholine | CH | CH | CH | CH | CH | H | H | H | H |
| 237 | (T₁=T₂ oxazole, O) | morpholine | CH | CH | CH | CH | CH | H | H | H | H |
| 238 | (T₁=T₂ pyridine) | morpholine | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 239 | (T1=CH, T2=CH, pyridine with N) | morpholine N-linked | CH | CH | CH | CH | CH | H | H | H | H |
| 240 | (T1=CH, T2=CH, pyridine isomer) | morpholine N-linked | CH | CH | CH | CH | CH | H | H | H | H |
| 241 | (T1=CH, T2=CH, pyridazine) | morpholine N-linked | CH | CH | CH | CH | CH | H | H | H | H |
| 242 | (T1=NH, T2=CH, dihydro) | morpholine N-linked | CH | CH | CH | CH | CH | H | H | H | H |
| 243 | (T1=CH, T2=CH, with NH) | morpholine N-linked | CH | CH | CH | CH | CH | H | H | H | H |
| 244 | (T1=CH, T2=CH, with NH) | morpholine N-linked | CH | CH | CH | CH | CH | H | H | H | H |
| 245 | (T1=CH, T2=CH, with NH) | morpholine N-linked | CH | CH | CH | CH | CH | H | H | H | H |
| 246 | (T1=N-Me, T2=CH) | morpholine N-linked | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 247 | | | CH | CH | CH | CH | CH | H | H | H | H |
| 248 | | | CH | CH | CH | CH | CH | H | H | H | H |
| 249 | | | CH | CH | CH | CH | CH | H | H | H | H |
| 250 | | | CH | CH | CH | CH | CH | H | H | H | H |
| 251 | | | CH | CH | CH | CH | CH | H | H | H | H |
| 252 | | | CH | CH | CH | CH | CH | H | H | H | H |
| 253 | | | CH | CH | CH | CH | CH | H | H | H | H |
| 254 | | | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 255 | T1/T2 pyridine | 4-cyanophenyl | CH | CH | CH | CH | CH | H | H | H | H |
| 256 | T1/T2 pyridine | 4-methoxyphenyl | CH | CH | CH | CH | CH | H | H | H | H |
| 257 | T1/T2 pyridine | 4-(trifluoromethoxy)phenyl | CH | CH | CH | CH | CH | H | H | H | H |
| 258 | T1/T2 pyridine | 4-methylpiperazin-1-yl | CH | CH | CH | CH | CH | H | H | H | H |
| 259 | T1/T2 pyridine | piperazin-1-yl | CH | CH | CH | CH | CH | H | H | H | H |
| 260 | T1/T2 pyridine | tetrahydropyran-4-yl | CH | CH | CH | CH | CH | H | H | H | H |
| 261 | T1/T2 pyridine | morpholin-4-yl | N | CH | CH | CH | CH | H | H | H | H |
| 262 | T1/T2 pyridine | 4-fluorophenyl | N | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 263 | T1,T2-pyridine | 4-Cl-phenyl | N | CH | CH | CH | CH | H | H | H | H |
| 264 | T1,T2-pyridine | 4-NC-phenyl | N | CH | CH | CH | CH | H | H | H | H |
| 265 | T1,T2-pyridine | 4-MeO-phenyl | N | CH | CH | CH | CH | H | H | H | H |
| 266 | T1,T2-pyridine | 4-F$_3$CO-phenyl | N | CH | CH | CH | CH | H | H | H | H |
| 267 | T1,T2-pyridine | 4-methylpiperazinyl | N | CH | CH | CH | CH | H | H | H | H |
| 268 | T1,T2-pyridine | piperazinyl | N | CH | CH | CH | CH | H | H | H | H |
| 269 | T1,T2-pyridine | tetrahydropyran-4-yl | N | CH | CH | CH | CH | H | H | H | H |
| 270 | T1,T2-pyridine | $^t$Bu | N | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 271 | T1=N, T2 pyridine | Ph | N | CH | CH | CH | CH | H | H | H | H |
| 272 | T1=N, T2 pyridine | morpholine-N | CH | CH | N | CH | CH | H | H | H | H |
| 273 | T1=N, T2 pyridine | 4-F-phenyl | CH | CH | N | CH | CH | H | H | H | H |
| 274 | T1=N, T2 pyridine | 4-Cl-phenyl | CH | CH | N | CH | CH | H | H | H | H |
| 275 | T1=N, T2 pyridine | 4-NC-phenyl | CH | CH | N | CH | CH | H | H | H | H |
| 276 | T1=N, T2 pyridine | 4-MeO-phenyl | CH | CH | N | CH | CH | H | H | H | H |
| 277 | T1=N, T2 pyridine | 4-F$_3$CO-phenyl | CH | CH | N | CH | CH | H | H | H | H |
| 278 | T1=N, T2 pyridine | 4-methylpiperazin-1-yl | CH | CH | N | CH | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 279 | T₁=N, T₂ pyridine | piperazine (HN) | CH | CH | N | CH | CH | H | H | H | H |
| 280 | T₁=N, T₂ pyridine | tetrahydropyran-4-yl | CH | CH | N | CH | CH | H | H | H | H |
| 281 | T₁=N, T₂ pyridine | ᵗBu | CH | CH | N | CH | CH | H | H | H | H |
| 282 | T₁=N, T₂ pyridine | Ph | CH | CH | N | CH | CH | H | H | H | H |
| 283 | T₁=N, T₂ pyridine | morpholinyl | CH | CH | CH | N | CH | H | H | H | H |
| 284 | T₁=N, T₂ pyridine | 4-F-C₆H₄ | CH | CH | CH | N | CH | H | H | H | H |
| 285 | T₁=N, T₂ pyridine | 4-Cl-C₆H₄ | CH | CH | CH | N | CH | H | H | H | H |
| 286 | T₁=N, T₂ pyridine | 4-NC-C₆H₄ | CH | CH | CH | N | CH | H | H | H | H |

-continued

| Ex | HET | X | Y | Z₁ | Z₂ | Z₃ | Z₄ | R₅ | R₆ | R₇ | R₈ |
|---|---|---|---|---|---|---|---|---|---|---|---|
| 287 | T₁=N, T₂ pyridine | 4-MeO-phenyl | CH | CH | CH | N | CH | H | H | H | H |
| 288 | T₁=N, T₂ pyridine | 4-F₃CO-phenyl | CH | CH | CH | N | CH | H | H | H | H |
| 289 | T₁=N, T₂ pyridine | 4-methylpiperazin-1-yl | CH | CH | CH | N | CH | H | H | H | H |
| 290 | T₁=N, T₂ pyridine | piperazin-1-yl | CH | CH | CH | N | CH | H | H | H | H |
| 291 | T₁=N, T₂ pyridine | tetrahydropyran-4-yl | CH | CH | CH | N | CH | H | H | H | H |
| 292 | T₁=N, T₂ pyridine | tBu | CH | CH | CH | N | CH | H | H | H | H |
| 293 | T₁=N, T₂ pyridine | Ph | CH | CH | CH | N | CH | H | H | H | H |
| 294 | T₁=N, T₂ pyridine | cyclohexyl | CH | CH | CH | CH | CH | H | H | H | H |

-continued

| Ex | HET | X | Y | $Z_1$ | $Z_2$ | $Z_3$ | $Z_4$ | $R_5$ | $R_6$ | $R_7$ | $R_8$ |
|---|---|---|---|---|---|---|---|---|---|---|---|
| 295 | (structure with $T_1$, $T_2$) | phenyl | CH | CH | CH | CH | CH | H | H | H | H |
| 296 | (structure with $T_1$, $T_2$) | $^t$Bu | CH | CH | CH | CH | CH | H | H | H | Me |
| 297 | (structure with $T_1$, $T_2$) | $^t$Bu | CH | CH | CH | CH | CH | H | H | Me | H |

Dosage and Administration

The present disclosure includes pharmaceutical composition for treating a subject having a neurological disorder comprising a therapeutically effective amount of a compound of Formulas (I) and (II), a derivative or a pharmaceutically acceptable salt thereof, and a pharmaceutically acceptable excipient, carrier or diluent. The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (IV) administration. The formulations for administration will commonly comprise a solution of the compound of the Formulas (I) and (II) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formulas (I) and (II) in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formulas (I) and (II) can be administered by introduction into the central nervous system of the subject, e.g., into the cerbrospinal fluid of the subject. The formulations for administration will commonly comprise a solution of the compound of Formulas (I) and (II) dissolved in a pharmaceutically acceptable carrier. In certain aspects, the compound of Formulas (I) and (II) is introduced intrathecally, e.g., into a cerebral ventricle, the lumbar area, or the cisterna magna. In another aspect, the compound of Formulas (I) and (II) is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formulas (I) and (II) is administered into a subject intrathecally. As used herein, the term "intrathecal administration" is intended to include delivering a pharmaceutical composition comprising a compound of Formulas (I) and (II) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formulas (I) and (II) to any of the above mentioned sites can be achieved by direct injection of the pharmaceutical composition comprising the compound of Formulas (I) and (II) or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formulas (I) and (II) is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formulas (I) and (II) with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formulas (I) and (II) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formulas (I) and (II) in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.01 to 100 mg per kilogram body weight of the recipient per day, preferably in the range of 0.1 to 10 mg per kilogram body weight per day. The desired dose is preferably presented once daily, but may be dosed as two, three, four, five, six or more sub-doses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated. Details on techniques for formulation and administration are well described in the scientific and patent literature, see, e.g., the latest edition of Remington's Pharmaceutical Sciences, Maack Publishing Co, Easton Pa. After a pharmaceutical composition has been formulated in an acceptable carrier, it can be placed in an appropriate container and labeled for treatment of an indicated condition. For administration of the compounds of Formulas (I) and (II), such labeling would include, e.g., instructions concerning the amount, frequency and method of administration.

Biological Examples

In Vitro Methods hPDE10A1 Enzyme Activity: 500 samples of serially diluted Human PDE10A1 enzyme were incubated with 50 µl of [$^3$H]-cAMP for 20 minutes (at 37° C.). Reactions were carried out in Greiner 96 deep well 1 ml master-block. The enzyme was diluted in 20 mM Tris HCl pH7.4 and [$^3$H]-cAMP was diluted in 10 mM $MgCl_2$, 40 mM Tris.HCl pH 7.4. The reaction was terminated by denaturing the PDE enzyme (at 70° C.) after which [$^3$H]-5'-AMP was converted to [$^3$H]-adenosine by adding 25 µl snake venom nucleotidase and incubating for 10 minutes (at 37° C.). Adenosine, being neutral, was separated from charged cAMP or AMP by the addition of 200 µl Dowex resin. Samples were shaken for 20 minutes then centrifuged for 3 minutes at 2,500 r.p.m. 50 µl of supernatant was removed and added to 200 µl of MicroScint-20 in white plates (Greiner 96-well Optiplate) and shaken for 30 minutes before reading on Perkin Elmer TopCount Scintillation Counter.

hPDE10A1 Enzyme Inhibition: To check inhibition profile 11 µl of serially diluted inhibitor was added to 50 µl of [$^3$H]-cAMP and 50 µl of diluted Human PDE10A1 and assay was carried out as in the enzyme activity assay. Data was analysed using Prism software (GraphPad Inc). Representative compounds of this disclosure are shown in the table below. A compound with the value "A" had an $IC_{50}$ value less than or equal to 200 nM. A compound with the value "B" had an $IC_{50}$ value less than or equal to 1000 nM:

| Ex | Name | hPDE10A1 $IC_{50}$ Band |
|---|---|---|
| 122 | (E)-2-(4-tert-butylphenyl)-N'-(isoquinolin-5-ylmethylene) cyclopropanecarbohydrazide | A |
| 195 | (E)-2-(4-tert-butylphenyl)-N'-(isoquinolin-5-ylmethylene) cyclopropanecarbohydrazide | B |
| 196 | (E)-2-(biphenyl-4-yl)-N'-(isoquinolin-5-ylmethylene)cyclopropanecarbohydrazide | A |
| 197 | (E)-2-(4-tert-butylphenyl)-N'-(1-(isoquinolin-5-yl)ethylidene)cyclopropanecarbohydrazide | B |
| 198 | (E)-2-(4-tert-butylphenyl)-N'-(isoquinolin-5-ylmethylene)-N-methylcyclopropanecarbohydrazide | A |

What is claimed is:

1. A compound of Formula (I) or (II)

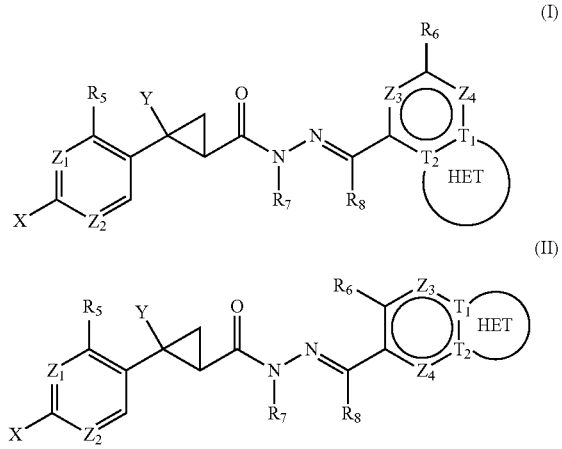

or a pharmaceutically acceptable salt thereof, wherein:

X is hydrogen, halogen, $C_3$-$C_8$ alkyl, $C_1$-$C_4$ alkoxy, optionally substituted cycloalkyl, optionally substituted cycloalkyloxy, optionally substituted cycloalkylalkyl, optionally substituted cycloalkylalkoxy, optionally substituted heterocycloalkyl, optionally substituted heterocycloalkylalkyl, optionally substituted heterocycloalkyloxy, optionally substituted phenyl, optionally substituted heteroaryl, optionally substituted heteroaryloxy or optionally substituted heteroarylalkyl;

Y is hydrogen, $C_3$-$C_8$ alkyl, $C_1$-$C_4$ alkoxy, optionally substituted cycloalkyl, optionally substituted cycloalkylalkyl, optionally substituted heterocycloalkyl, optionally substituted heterocycloalkylalkyl, optionally substituted phenyl or optionally substituted heteroaryl;

$T_1$ is C;
$T_2$ is C;
$Z_1$ is $CR_1$ or N;
$Z_2$ is $CR_2$ or N;
$Z_3$ is $CR_3$ or N;
$Z_4$ is $CR_4$ or N;

HET is (i) an optionally substituted monocyclic heteroaryl having 5 ring atoms selected from the group consisting of C, O, S and N provided the total number of ring heteroatoms is less than or equal to three and wherein no more than one of the total number of heteroatoms is oxygen or sulfur, (ii) an optionally substituted monocyclic heteroaryl having 6 atoms selected from the group consisting of C and N provided that not more than 2 ring atoms are N, or (iii) an optionally substituted monocyclic heterocycloalkyl;

$R_1$ is hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido;

$R_2$ is hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido;

$R_3$ is hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido;

$R_4$ is hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido;

$R_5$ is hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido;

$R_6$ is hydrogen, halogen, $C_1$-$C_4$ alkyl, optionally substituted $C_3$-$C_6$ cycloalkyl, $C_1$-$C_4$ alkoxy, optionally substituted $C_3$-$C_6$ cycloalkyloxy, cyano, amino, alkylamino, dialkylamino, alkylsulfonyl, carboxy, nitro amido, alkylamido or dialkylamido;

$R_7$ is hydrogen, $C_1$-$C_4$ alkyl or optionally substituted $C_3$-$C_6$ cycloalkyl; and $R_8$ is hydrogen, $C_1$-$C_4$ alkyl or optionally substituted $C_3$-$C_6$ cycloalkyl.

2. The compound of claim 1 wherein $R_7$ is hydrogen or $C_1$-$C_4$ alkyl; or a pharmaceutically acceptable salt thereof.

3. The compound of claim 1 wherein $R_8$ is hydrogen or $C_1$-$C_4$ alkyl; or a pharmaceutically acceptable salt thereof.

4. The compound of claim 1 wherein $R_5$ is hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano or alkylsulfonyl; or a pharmaceutically acceptable salt thereof.

5. The compound of claim 1 wherein $R_6$ is hydrogen, halogen, $C_1$-$C_4$ alkyl, $C_3$-$C_6$ cycloalkyl, $C_1$-$C_4$ alkoxy, $C_3$-$C_6$ cycloalkyloxy, cyano or alkylsulfonyl; or a pharmaceutically acceptable salt thereof.

6. The compound of claim 1 wherein Y is $C_3$-$C_6$ cycloalykl, $C_4$-$C_7$ cycloalkylalkyl, $C_4$-$C_7$ cycloalkylalkoxy, heterocycloalkyl, or heterocycloalkyloxy; or a pharmaceutically acceptable salt thereof.

7. The compound of claim 1 wherein X is alkyl, phenyl or heteroaryl; or a pharmaceutically acceptable salt thereof.

8. The compound of claim 1 wherein HET is a monocyclic heterocycloalkyl; or a pharmaceutically acceptable salt thereof.

9. The compound of claim 8 wherein HET is a monocyclic heterocycloalkyl having only 6 ring atoms; or a pharmaceutically acceptable salt thereof.

10. The compound of claim 8 wherein HET is a monocyclic heterocycloalkyl having only 5 ring atoms; or a pharmaceutically acceptable salt thereof.

11. The compound of claim 1 wherein HET is imidazolyl, thiazolyl, oxazolyl, pyridinyl, pyrmidinyl, pyrazinyl, triazolyl, pyrazolyl, cinnolinyl, piperdinyl, pyrrolidinyl, tetrahydrofuranyl, or pyranyl; or a pharmaceutically acceptable salt thereof.

12. A method for treating a CNS disorder comprising administering to a human a therapeutically effective amount of a pharmaceutical composition comprising the compound of any one of claims 1, 2, 3, 4, 5, 6, 7, and 8-11 or a pharmaceutically acceptable salt thereof and a pharmaceutically acceptable carrier or excipient.

13. A method for treating eating disorders, obesity, compulsive gambling, sexual disorders, narcolepsy, sleep disorders, diabetes, metabolic syndrome or for use in smoking cessation treatment comprising administering to a human thereof a therapeutically effective amount of a pharmaceutical composition comprising the compound of any one of claims 1, 2, 3, 4, 5, 6, 7 and 8-11 or a pharmaceutically acceptable salt thereof and a pharmaceutically acceptable carrier or excipient.

14. A method for treating obesity, schizophrenia, schizoaffective conditions, Huntington's disease, dystonic conditions and tardive dyskinesia comprising administering to a human thereof a therapeutically effective amount of a pharmaceutical composition comprising the compound of any one of claims 1, 2, 3, 4, 5, 6, 7 and 8-11 or a pharmaceutically acceptable salt thereof and a pharmaceutically acceptable carrier or excipient.

* * * * *

UNITED STATES PATENT AND TRADEMARK OFFICE
CERTIFICATE OF CORRECTION

PATENT NO.       : 8,481,532 B2  
APPLICATION NO. : 13/002922  
DATED            : July 9, 2013  
INVENTOR(S)      : Ripka et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 214 days.

Signed and Sealed this
Eighth Day of September, 2015

Michelle K. Lee
*Director of the United States Patent and Trademark Office*